US012784888B2

(12) United States Patent
Khalil

(10) Patent No.: US 12,784,888 B2
(45) Date of Patent: Nov. 3, 2026

(54) INFUSION PUMP PROGRAMMING SYSTEM WITH AUTOMATED DOSE EVALUATION, REAL-TIME INFUSION RATE CALIBRATION, AND SAFETY VALIDATION

(71) Applicant: Ahmed Fahd Khalil, Friendswood, TX (US)

(72) Inventor: Ahmed Fahd Khalil, Friendswood, TX (US)

( * ) Notice: Subject to any disclaimer, the term of this patent is extended or adjusted under 35 U.S.C. 154(b) by 0 days.

(21) Appl. No.: 19/342,578

(22) Filed: Sep. 28, 2025

(65) Prior Publication Data

US 2026/0094687 A1 Apr. 2, 2026

(51) Int. Cl.

*G16H 20/17* (2018.01)
*A61M 5/142* (2006.01)
*G16H 40/40* (2018.01)
*G16H 40/67* (2018.01)

(52) U.S. Cl.

CPC ............ *G16H 20/17* (2018.01); *A61M 5/142* (2013.01); *G16H 40/40* (2018.01); *G16H 40/67* (2018.01); *A61M 2005/14208* (2013.01); *A61M 2205/3389* (2013.01); *A61M 2205/3584* (2013.01); *A61M 2205/502* (2013.01); *A61M 2205/52* (2013.01); *A61M 2205/6072* (2013.01); *A61M 2205/6081* (2013.01); *A61M 2205/702* (2013.01)

(58) Field of Classification Search

CPC ........ G16H 20/17; G16H 40/40; G16H 40/67; G16H 40/63; A61M 5/142; A61M 2005/14208; A61M 2205/3389; A61M 2205/3584; A61M 2205/502; A61M 2205/52; A61M 2205/6072; A61M 2205/6081; A61M 2205/702

USPC .......................................................... 705/2, 3

See application file for complete search history.

(56) References Cited

U.S. PATENT DOCUMENTS 4,785,799 A * 11/1988 Schoon ................. A61M 5/172 604/151
5,219,330 A * 6/1993 Bollish ................. A61M 5/172 604/151
5,609,575 A * 3/1997 Larson .................. G16H 20/17 604/65

(Continued)

*Primary Examiner* — Jason S Tiedeman

(74) *Attorney, Agent, or Firm* — Novel Patent Services LLC

(57) ABSTRACT

An infusion pump programming system with automated dose evaluation, real-time infusion rate calibration, and safety validation. The infusion pump programming system comprises a computing device having a processor and a memory for storing instructions that are executed by the processor. The computing device is communicatively coupled with a server via a network. The infusion pump programming system automates recalibration of multi-step infusion protocols whenever rate, volume, or total infusion time is modified, eliminating manual re-entry and reducing evaluation errors. The infusion pump programming system preserves clinical logic and sequencing of infusion steps such as ramp-up, main infusion, ramp-down, and flush phases ensuring that safety thresholds and dosing rules remain intact during reevaluation. The infusion pump programming system has wide commercial applicability across hospitals, outpatient centers, pharmacies, and home-care infusion services. The infusion pump programming system substantially reduces staff time spent on manual infusion evaluations and documentation.

18 Claims, 14 Drawing Sheets

(56) References Cited

U.S. PATENT DOCUMENTS

| | | | | | |
|---|---|---|---|---|---|
| 5,772,635 | A * | 6/1998 | Dastur | G16H 20/17 | |
| | | | | 604/67 | |
| 8,234,128 | B2 * | 7/2012 | Martucci | A61B 5/4839 | |
| | | | | 705/2 | |
| 8,775,196 | B2 * | 7/2014 | Simpson | A61B 5/746 | |
| | | | | 705/2 | |
| 8,882,701 | B2 * | 11/2014 | DeBelser | A61M 5/14244 | |
| | | | | 604/67 | |
| 9,501,619 | B2 * | 11/2016 | Portnoy | G06Q 10/1093 | |
| 10,173,008 | B2 * | 1/2019 | Simpson | G16H 10/60 | |
| 12,653,944 | B2 * | 6/2026 | Marsh | A61M 5/1408 | |
| 2005/0086008 | A1 * | 4/2005 | DiGianfilippo | G07F 13/06 | |
| | | | | 702/19 | |
| 2011/0137239 | A1 * | 6/2011 | DeBelser | G16H 20/17 | |
| | | | | 604/67 | |
| 2014/0235984 | A1 * | 8/2014 | Wilbur | A61B 5/150259 | |
| | | | | 600/365 | |
| 2014/0288947 | A1 * | 9/2014 | Simpson | G16H 40/67 | |
| | | | | 705/2 | |
| 2016/0287784 | A1 * | 10/2016 | Straw | A61M 5/14236 | |
| 2018/0085520 | A1 * | 3/2018 | Ledford | A61M 5/14228 | |
| 2020/0206414 | A1 * | 7/2020 | Marsh | A61M 5/1408 | |
| 2022/0362463 | A1 * | 11/2022 | Lindo | A61M 5/16827 | |
| 2022/0370716 | A1 * | 11/2022 | Martin | A61M 5/007 | |
| 2024/0299651 | A1 * | 9/2024 | Sadleir | A61M 5/284 | |
| 2024/0390582 | A1 * | 11/2024 | Drost | G16H 40/63 | |

* cited by examiner

1000

108

| [QR CODE] | **Specialty pharmacy infusion pump sheet**<br>Pump settings: Variable | |
|---|---|---|
| **PATIENT INFORMATION** | | |
| Patient Name: DEMO | Patient ID: DEMO | DOB: 12/31/2024 |

Drug Name: DEMO MEDICATION: Sig: DEMO DIRECTIONS
Remove volume: REMOVE DEMO VOLUME
Prime volume: 10 mL
Total volume to be infused: 140.0 mL

The pump is already PROGRAMMED:
• Turn pump on to review settings • Wait for warmup phase to stop • Press enter • Press enter to 'repeat RX' • Pump will automatically go through programming steps • Then press 'Run' to start infusion

| Step | Rate / time | Volume |
|---|---|---|
| 1st | 25 ml/hr x 30 min | 12.5 ml |
| 2nd | 75 ml/hr x 30 min | 37.5 ml |
| 3rd | 125 ml/hr x 30 min | 62.5 ml |
| 4th | 137 ml/hr x 165.328467 min | 377.5 ml |
| 5th | 137 ml/hr x 4.379562 min | 10 ml (flush) |

Total infusion time: 1 hour and 20 minutes

| Program written by: DEMO PHARMACIST | Date: 12/31/2024 |
|---|---|

FIG. 10

INFUSION PUMP PROGRAMMING SYSTEM WITH AUTOMATED DOSE EVALUATION, REAL-TIME INFUSION RATE CALIBRATION, AND SAFETY VALIDATION

FIELD OF INVENTION

The present disclosure relates generally to infusion pump programming systems, and more particularly to an infusion pump programming system that automatically recalibrates infusion parameters when infusion rate or total infusion time is modified, while maintaining clinical safety constraints.

BACKGROUND

Intravenous (IV) infusion therapy often involves medication dosing that must be tailored to individual patient parameters, such as weight, clinical indication, and treatment regimen. The preparation of infusion protocols especially those involving weight-based dosing, multi-step infusion sequences, drug dilution, vial waste minimization, and pump programming requires numerous mathematical steps that are routinely performed manually by pharmacists, nurses, and clinicians. These manual evaluations are time-consuming and prone to human error, leading to risks of incorrect dose delivery, adverse drug events, improper infusion rates, and incomplete clinical documentation.

Errors in infusion therapy preparation commonly occur during several critical stages, including medication dose evaluation particularly when performing mg/kg conversions, unit normalization, and cumulative dose computations vial selection and drug compounding involving concentration determination, diluent volume measurements, and removal of excess solution from pre-filled infusion bags, as well as during the programming of multi-rate and multi-step infusion protocols such as ramp-up, main, ramp-down, and flush phases. Additional errors frequently arise during the transcription and documentation of pump programming sheets, where manual entry increases the risk of inaccuracies.

These types of errors may result in dose deviations, patient harm, unnecessary drug wastage especially with high-cost biologics and chemotherapeutic agents and failure to comply with clinical and regulatory standards. Multi-step intravenous infusion protocols generally require a specific sequence of steps, including a pre-infusion flush, one or more ramp-up infusion steps, a main infusion step, one or more ramp-down steps, and a post-infusion flush, all of which must be executed in a precise clinical order to ensure safe and effective drug administration.

In current clinical practice, modifying an infusion parameter such as the total infusion time or the infusion rate requires manual reevaluation of all individual step durations or rates within a multi-step protocol. Conventional infusion calculators are limited to computing values for a single infusion step and lack the ability to dynamically recalibrate an entire multi-step infusion schedule. Existing tools generally either require complete re-entry of all infusion steps or perform a basic proportional scaling of step parameters, which often violates clinical safety rules. As a result, ramp-up steps may no longer follow a gradual increase, ramp-down steps may exceed safe dosing levels, and clinically critical steps may be reduced below minimum required durations. These shortcomings lead to a heightened risk of dosing errors, clinically unsafe infusion sequences, and significant time spent on manual reevaluation of step-by-step adjustments. Further, current systems do not provide automated validation mechanisms to ensure that recalculated sequences remain within clinical and safety constraints. Consequently, there is no known prior art that enables intelligent recalibration of multi-step infusion protocols while preserving the required clinical logic, safety thresholds, and sequencing rules necessary for safe intravenous medication administration.

Several digital tools and electronic medical record (EMR)-integrated calculators have been introduced to assist with infusion dosing and pump programming. Static infusion rate calculators that compute single-step infusion rates based on volume and time inputs. Drug monograph-based dosing guidelines embedded in EMRs or clinical decision support systems (CDSS). Spreadsheet-based dosing calculators used in hospital pharmacies for dose, volume, and concentration computations. Smart infusion pumps with drug libraries that enforce programmed limits and reduce bedside programming errors. Basic compounding software that provides dose preparation instructions and logs compounding steps.

Despite these advancements, existing solutions suffer from significant shortcomings such as lack of integrated workflow, no dynamic calibration capability, inadequate multi-step protocol automation, limited or no waste optimization, weak validation and safety controls, and incomplete documentation automation. Existing tools operate in silos dose calculators do not integrate with vial optimization, infusion step programming, or document generation, requiring multiple systems and manual transcription between them. Conventional systems do not allow recalibration of infusion protocols once calculated; changes to rate or time require full manual re-evaluation, introducing error risk. Multi-phase infusions (ramp-up, main, ramp-down, flush) must typically be calculated manually, as most systems only support single-rate infusion computation. Current tools do not apply algorithmic vial combination optimization, causing high drug wastage, especially for expensive biologics and chemotherapy agents supplied in multiple vial sizes. Many systems lack real-time dose-range validation, concentration checks, and infusion-rate safety logic, leading to unsafe programming. Most solutions require pharmacists to manually type pump programming sheets, leading to transcription errors and inconsistent formatting.

Conventional infusion programming and dose calculation systems typically rely on static computation of infusion parameters, in which rate, volume, and duration are manually entered or computed only once at the time of prescription. When any parameter is modified such as a rate adjustment due to patient response or clinical requirement these systems do not automatically recalibrate the dependent parameters while preserving total volume. This limitation requires manual re-entry and verification, which introduces risk of rounding error, incorrect dose delivery, and noncompliance with pump-specific constraints.

Existing hospital pharmacy compounding tools and infusion pump controllers are often unidirectional in nature, supporting only forward computation (from rate to duration) or fixed infusion templates. They lack a bidirectional calibration capable of adjusting both rate and duration while enforcing mathematical volume invariance. Similarly, prior art systems do not perform synchronized recalibration across multi-step infusion profiles; changes to one step typically break total duration alignment or disrupt step hierarchy.

Some electronic medical record (EMR) or drug library software provide dose verification functions, but these rely on threshold-based validation or static formula checks rather than multi-layer algorithmic validation. Such systems are not equipped to execute real-time, multi-layer validation architecture that accounts for step synchronization, volume tolerance, duration tolerance, and cumulative rounding control in one integrated computational pipeline.

In addition, prior systems do not employ deterministic floating-point precision, resulting in small but clinically significant deviations when converting between rate, duration, and volume. They also lack an integrated rate synchronization that preserves clinical logic across ramp-up, main, and ramp-down steps after recalibration. As a result, recalculated infusion programs in prior art may yield inconsistent total durations, incomplete volume delivery, or abrupt rate transitions.

Therefore, there is a need for an infusion pump programming system that automatically recalibrates infusion parameters when infusion rate or total infusion time is modified, while maintaining clinical safety constraints. Further, there is a need for a infusion pump programming system that can intelligently and automatically recalibrate multi-step infusion schedules when any infusion parameter is modified, maintain the clinical logic of ramp-up, main, and ramp-down phases, prevent violation of safety thresholds, eliminate manual re-entry of infusion steps, and provide automated real-time validation to ensure safe and accurate infusion programming.

SUMMARY OF THE INVENTION

The following presents a simplified summary of one or more embodiments of the present disclosure to provide a basic understanding of such embodiments. This summary is not an extensive overview of all contemplated embodiments and is intended to neither identify key nor critical elements of all embodiments, nor delineate the scope of any or all embodiments.

The present disclosure, in one or more embodiments, relates to an infusion pump programming system with automated dose evaluation, real-time infusion rate calibration, and safety validation. The infusion pump programming system comprises a computing device having a processor and a memory for storing instructions that are executed by the processor. The computing device is communicatively coupled with a server via a network.

In one embodiment herein, the server comprises a database, which comprises medication identifiers, vial strengths, standardized dosing protocols, and infusion safety limits. The server is configured to store historical infusion data and provides version control of the generated infusion protocols. The database includes pediatric, adult, renal-adjusted, and condition-specific dosing protocols.

In one embodiment herein, the processor is configured to receive input parameters including patient-specific data, and infusion parameters through a user interface. In one embodiment, the user interface is configured to display a validation passed message upon successful verification of the infusion protocol. The message comprises confirmation that all infusion steps are valid, a total volume evaluation showing equivalence between a sum of step volumes and target infusion volume, and a total duration evaluation showing equivalence between a sum of step durations and expected total infusion time.

In one embodiment herein, the processor is configured to execute a dose evaluation module to compute a required drug amount based on patient-specific data. The patient-specific data comprises at least patient weight and prescribed dose.

In one embodiment herein, the processor is configured to execute a protocol generation module to generate an initial infusion protocol for at least one of a fixed-rate infusion protocol, and a multi-step variable-rate infusion protocol. The initial infusion protocol comprises a plurality of infusion steps, each step defining at least an infusion rate and a duration.

In one embodiment herein, the protocol generation module automatically determines a missing infusion parameter when any two of infusion rate, infusion volume, and infusion duration are provided.

In one embodiment herein, the processor is configured to classify the plurality of infusion steps into step types including a pre-infusion flush, one or more ramp-up steps, a main infusion step, one or more ramp-down steps, and a post-infusion flush.

In one embodiment herein, the processor is configured to receive a calibration command, through a calibration module, selecting at least one of a rate calibration mode in which a new infusion rate is applied, and a time calibration mode in which a new total infusion duration is applied. The calibration module is configured to receive the calibration command from a mode selector, which is configured to enable a user to select between the rate calibration mode and the time calibration mode.

In one embodiment herein, the calibration module is configured to recalculate the infusion parameters of the plurality of infusion steps based on the selected calibration mode while preserving at least one of total infusion volume when recalibrating time or rate, and total infusion duration when recalibrating infusion rate or volume.

In one embodiment herein, the calibration module is configured to apply a recalibration process configured to maintain clinical infusion logic during recalibration. The calibration module comprises the rate calibration mode configured to recalculate infusion durations while preserving infusion volumes. The calibration module comprises the time calibration mode configured to recalculate infusion rates while preserving infusion volumes. The calibration module performs deterministic bottom-up aggregation by computing total duration and total volume exclusively from individual step parameters, thereby eliminating floating-point drift.

In one embodiment herein, in the rate calibration mode is configured to recalculate the duration for one or more of the plurality of infusion steps based on the new infusion rate while holding the calculated volume for each step constant, thereby modifying the total infusion duration while preserving the total infusion volume and the defined sequential order.

In one embodiment herein, in the time calibration mode is configured to recalculate the infusion rate for one or more of the plurality of infusion steps based on the new total infusion duration while holding the calculated volume for each step constant, thereby modifying the infusion rate while preserving the total infusion volume and the defined sequential order.

In one embodiment herein, the recalculating maintains a predetermined clinical step hierarchy among the ramp-up steps, the main infusion step, and the ramp-down steps stored in the database, wherein the clinical step hierarchy comprises pre-infusion flush, ramp-up, main infusion, ramp-down, and post-infusion flush.

In one embodiment herein, the calibration module performs device-compatibility rounding of step volumes to 0.0 or 0.5 increments and redistributes the resulting volume difference to a designated compensation step while maintaining total-volume invariance.

In one embodiment herein, the calibration module implements a single-pass convergence through constraint enforcement during calculation construction. The single-pass convergence process produces, in a single computational traversal, recalibrated rate and duration values using non-iterative closed-form equations, thereby preventing floating-point drift and eliminating intermediate unsafe states. The single-pass convergence comprises computing a plurality of recalibrated rates and duration values in a single, non-iterative traversal using closed-form equations.

The infusion pump programming system is configured to explicitly lock medication volumes before parameter adjustment, enforce time distribution exactness through mathematical derivation, and apply rate synchronization through an atomic assignment. All validation criteria are satisfied by construction during a single computational pass without requiring iterative refinement. The calibration module performs the atomic assignment that simultaneously writes the same infusion rate value to both the main infusion step and the flush step.

In one embodiment herein, the processor is configured to execute a validation module to validate the recalibrated infusion protocol for clinical safety and mathematical consistency prior to execution. The validation module provides visual indicators that comprise a green check for valid parameters and a red warning symbol for invalid parameters. The validation module is configured to apply tolerance limits of ±0.1 mL for total volume and ±1 minute for total infusion duration.

In one embodiment herein, the processor is configured to execute a document generation module to generate an infusion output that includes patient information, infusion parameters, and a graphical code. The document generation module generates a document containing a QR code encoding infusion parameters in a structured data format.

In one embodiment herein, the infusion pump programming system comprises a vial optimization module, which is configured to receiving a required dose value for a selected medication, retrieving available vial sizes including strength values from the database, generate a plurality of vial combinations up to a predefined maximum vial count, calculating, for each vial combination, total drug amount, waste amount, and waste percentage, and ranking the vial combinations based on minimum waste percentage, and displaying an optimal vial combination to a user based on the ranking. The vial preparation assistance module constrains vial selection to combinations that satisfy pump-device requirements for minimum measurable volume, minimum programmable rate, infusion-time tolerances, and drug-stability duration, thereby producing only clinically usable and pump-compatible vial configurations.

In one embodiment herein, the vial optimization module implements a multi-strategy dynamic optimization engine configured to generate vial combinations using four parallel optimization strategies simultaneously, rank combinations using dual-criteria global optimization prioritizing waste minimization primarily and vial count reduction secondarily, integrate supply-period optimization across entire treatment duration, employ intelligent thresholds triggering alternative suggestions at 20% waste and optimize accuracy boundaries (95-105%), and utilize precision remainder detection with 0.01 clinical significance threshold.

In one embodiment, the processor generates a pump-executable control-register sequence and writes recalibrated rate, duration, and step-transition parameters directly into device-specific infusion-pump registers in a single atomic update, thereby preventing transient unsafe intermediate states during reprogramming. The single atomic update comprises simultaneous updating of the main infusion rate and flush rate such that no intermediate mismatched values are stored in the memory.

In one embodiment, the infusion pump programming system is configured to enable dynamic insertion of additional infusion steps, and upon adding a new step. The processor automatically assigns a sequential step number, allocates default parameter values for rate, volume, and duration based on step type, and recalculates overall protocol sequencing to maintain correct clinical order.

In one embodiment herein, a method for recalibrating multi-step infusion protocols using the infusion pump programming system. At first step, the initial infusion protocol with a plurality of steps classified by type is provided by the protocol generation module. Next, the calibration command is received by the calibration module to change at least one of infusion rate, and total infusion duration. Next, recalibration is performed to modify only non-locked steps while preserving step order, clinical logic, clinical step hierarchy, and minimum step durations. Next, the recalibrated protocol is validated for dose safety and infusion accuracy by the validation module. Later, the recalibrated protocol is provided for programming an infusion pump.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

The accompanying drawings, which are incorporated in and constitute a part of the specification, illustrate an embodiment of the invention, and, together with the description, explain the principles of the invention.

FIG. 10 illustrates a layout depicting a document generation process, which is displayed on the user interface, in accordance with embodiments of the invention.

DETAILED DESCRIPTION

Figure 1:
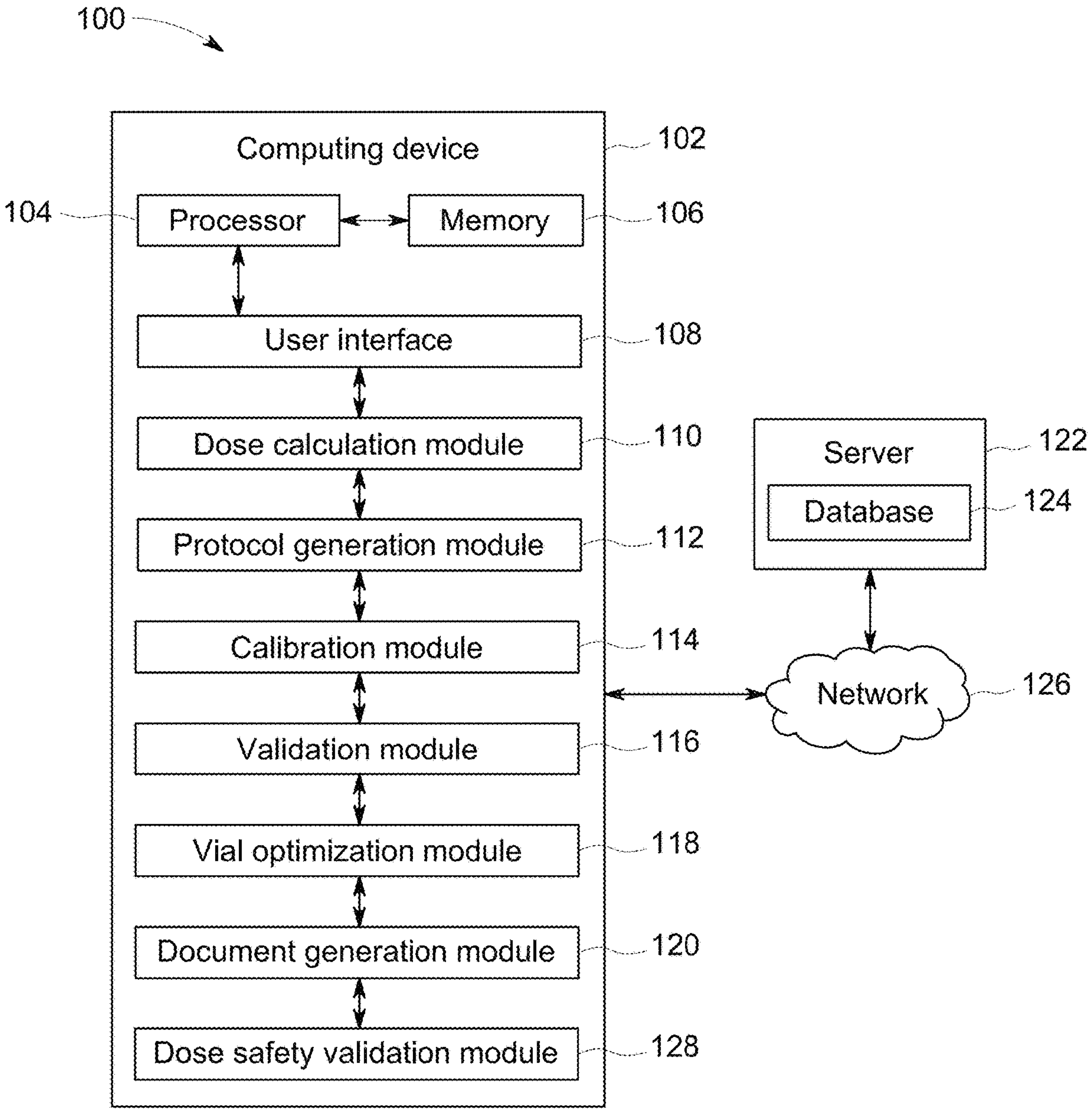
FIG. 1 illustrates a block diagram of a infusion pump programming system with automated dose evaluation, real-time infusion rate calibration, and safety validation, in accordance with embodiments of the invention.

Reference will now be made in detail to the present preferred embodiments of the invention, examples of which are illustrated in the accompanying drawings. Wherever possible, the same reference numerals are used in the drawings and the description to refer to the same or like parts.

FIG. 1 refers to a block diagram of an infusion pump programming system 100 for recalibrating multi-step infusion protocols. The infusion pump programming system 100 comprises a computing device 102 having a processor 104 and a memory 106 for storing instructions that are executed by the processor 104. The computing device 102 is communicatively coupled with a server 122 via a network 126.

In one embodiment, the server 122 comprises a database 124, which comprises medication identifiers, vial strengths, standardized dosing protocols, and infusion safety limits. The server 122 is configured to store historical infusion data and provides version control of the generated infusion protocols. The database 124 includes pediatric, adult, renal-adjusted, and condition-specific dosing protocols.

In one embodiment, the database 124 is configured to store structured medication information, The database 124 comprises, for each medication, at least one of identification attributes, available dose forms and vial configurations with associated strength and volume parameters, preparation, reconstitution, or dilution instructions, concentration and administration safety limits, standardized or recommended infusion protocols, and dosing guidance for different patient groups or clinical conditions. The database 124 is further configured to accommodate both pre-configured medication records and user-defined medication entries, and to persistently store such data using a local or remote storage mechanism. In one embodiment, the term "medication" broadly refers to a drug or pharmaceutical substance intended for use in the diagnosis, treatment, mitigation, cure, or prevention of a disease or medical condition.

In a preferred embodiment, the database 124 stored in a structured JSON format. The database 124 comprises medication identification data includes brand name, generic name, and National Drug Code (NDC) information, multiple vial size configurations specifying strength, unit, and volume parameters, reconstitution instructions and dilution requirements; maximum allowable concentration limits for safe administration, predefined fixed-rate infusion protocols for selected medications, and special dosing regimens adapted for different patient groups. The database 124 is configured to store both pre-loaded medication records and user-defined custom medication entries, and is persistently maintained using a cloud-based storage service.

The network 126 acts as a communication that allows the computing device 102 to interact with the other components of the infusion pump programming system 100, thereby facilitating the exchange of data, commands, and information. In one embodiment herein, the network 126 can be a wireless communication infrastructure, which offers the users flexibility and convenience when interacting with the infusion pump programming system 100. This wireless connectivity enables the users to access the infusion pump programming system 100 from various locations, without being tethered to a fixed physical connection.

In one embodiment herein, the network 126 can be, but not limited to, local area network (LAN), cellular network, wide area network (WAN), intranet, virtual private network (VPN), and wireless networks that use radio frequency (RF) or infrared (IR) technology to transmit data without the need for physical cables, thereby providing mobility and flexibility. The versatility of the network 126 ensures that the computing device 102 can seamlessly connect to the server 122 and the database 124, thereby enabling the users to access the infusion pump programming system's 100 functionalities and resources from a variety of locations and devices. This wireless connectivity enhances the overall accessibility and convenience of the infusion pump programming system 100 for the users.

In one embodiment, the processor 104 acts as the central processing unit (CPU) of the infusion pump programming system 100, responsible for coordinating different tasks and carrying out complex operations, data processing, and decision-making by fetching instructions from the memory 106, thereby decoding the instructions and executing the necessary actions.

In one embodiment herein, the memory 106 serves as the storage component of the infusion pump programming system 100, holding the executable instructions, as well as any data or information required by the processor 104 to perform its tasks. The data includes user inputs, system configurations, and any other relevant data needed for the infusion pump programming system's operations. Through the communication between the processor 104 and the memory 106, the infusion pump programming system 100 is able to process the user inputs, access stored information, perform computations, and make decisions accordingly.

In one embodiment herein, the computing device 102 represents any electronic device that the user can utilize to interact with the infusion pump programming system 100. The computing device 102 can be, but not limited to, a smartphone, a laptop, a tablet, a personal computer, or any other suitable electronic device. The computing device 102 serves as the user's gateway to accessing and interacting with the infusion pump programming system 100. The computing device 102 is configured to enable the user to engage with the infusion pump programming system's functionalities and capabilities through a user interface 108.

In one embodiment herein, the user interface 108 is a crucial component of the computing device 102, which allows the users to input commands, receive information, and control the infusion pump programming system 100. The user interface 108 can be, but not limited to, a touch screen, a keyboard, a mouse, voice recognition modules, gesture recognition sensors, and virtual reality interfaces. The versatility of the user interface 108 ensures that the users can engage with the infusion pump programming system 100 in a manner that is most intuitive and comfortable for the users, thereby catering to a wide range of user preferences and accessibility needs. The computing device 102 empowers the users to interact with the infusion pump programming system 100 seamlessly and efficiently by providing multiple user interface options, thereby leveraging the most appropriate input and output modalities for their specific needs and preferences.

In one embodiment, the processor 104 is configured to receive input parameters including patient-specific data, and infusion parameters through the user interface 108. The user interface 108 includes input locking to prevent modifications after validation and document generation. In some embodiments, the hardware-ready command sequence is formatted in a structure compatible with pump firmware command registers, including rate-control, duration-control, and step-transition registers. This eliminates intermediate user programming inputs and prevents transient inconsistent rate states.

In one embodiment, the processor 104 is configured to execute a dose evaluation module 110 to compute a required drug amount based on patient-specific data. The patient-specific data comprises at least patient weight and prescribed dose.

In a preferred embodiment, the dose evaluation module 110 is configured to perform multi-parameter dose and infusion evaluations based on the input parameters including patient weight with automatic unit conversion between kilograms and pounds, dose amount and unit expressed in mg/kg, units/kg, or as a fixed dose, dose frequency expressed as daily, weekly, bi-weekly or other defined intervals, number of days of supply required; total infusion volume; prime volume to account for infusion line capacity, flush volume for post-infusion clearing of the line, total infusion time expressed in hours and minutes, and an infusion mode indicating whether overfill is to be removed or whether the drug solution is to be added to an empty infusion container.

The dose evaluation module 110 is configured to execute at least the following computation methods: weight-based dosing evaluations, concentration determination evaluations, and volume distribution evaluations, as described below.

In the weight-based dosing evaluations, the dose evaluation module 110 is configured to compute:

$$\text{Single Dose} = (\text{Dose Rate} \times \text{Patient Weight})$$

$$\text{Daily Dose} = (\text{Single Dose} \times \text{Dose Frequency})$$

$$\text{Total Drug Required} = (\text{Daily Dose} \times \text{Days of Supply})$$

In the concentration determination evaluations, the dose evaluation module 110 is further configured to compute:

$$\text{Drug Concentration} = \frac{\text{Total Drug Amount}}{\text{Total Infusion Volume}}$$

$$\text{Infusion Rate} = \frac{\text{Total Infusion Volume}}{\text{Total Infusion Time}}$$

In the volume distribution evaluations, the dose evaluation module 110 is further configured to compute:

$$\text{Drug Volume} = \frac{\text{Total Drug Amount}}{\text{Drug Concentration}}$$

-continued $$\text{Diluent Volume} = (\text{Total Infusion Volume} - \text{Drug Volume})$$

$$\text{Final Infusion Volume} = (\text{Total Infusion Volume} - \text{Prime Volume})$$

In another embodiment, the dose evaluation module 110 is configured to process a plurality of dosing and infusion-related input parameters and to compute drug quantity, concentration, and infusion delivery characteristics accordingly. The input parameters may include one or more of patient-specific attributes, prescribed dose information, dosing frequency, treatment duration, infusion volume values, priming and flushing volumes, infusion time, and infusion preparation mode.

The dose evaluation module 110 is further configured to determine, based on the input parameters, one or more of patient-adjusted dose quantities, total drug requirement over a treatment period, resulting concentration for preparation of the infusion, infusion rate or time to achieve the prescribed administration schedule, and volume allocation between drug solution, diluent, and ancillary volumes. The dose evaluation module 110 may further adjust calculated values based on infusion preparation mode to account for overfill or alternative container preparation techniques.

In one embodiment, the processor 104 is configured to execute a protocol generation module 112 to generate an initial infusion protocol for at least one of a fixed-rate infusion protocol, and a multi-step variable-rate infusion protocol. The initial infusion protocol comprises a plurality of infusion steps, each step defining at least an infusion rate and a duration. In one embodiment, the protocol generation module 112 automatically determines a missing infusion parameter when any two of infusion rate, infusion volume, and infusion duration are provided.

In a preferred embodiment, the protocol generation module 112 is configured to determine a missing infusion parameter when any two of infusion rate (mL/hr), infusion volume (mL), and infusion duration (minutes) are provided. The protocol generation module 112 implements a triangular computational relationship among rate, volume, and time by applying the following equations:

$$\text{Rate } (R) = \text{volume } (V)/(\text{duration } (T)/60)$$

$$V = (R \times T)/60$$

$$T = (V/R) \times 60$$

In one embodiment, the processor 104 implements a triangular computational relationship through the protocol generation module 112 that allows for the dynamic reevaluation of dependent infusion parameters based on the preserved constraint of total infusion volume. The processor 104 automatically selects the appropriate calculation mode based on the user-provided input parameters, ensuring the consistent application of mathematical relationships between rate, volume, and duration.

Mode 1: Rate and Duration Known→Calculate Volume: When the infusion rate and duration are provided, the processor 104 calculates the infusion volume using the formula:

For example, if the user inputs a rate of 100 mL/hr and a duration of 30 minutes, the processor 104 calculates the infusion volume as:

$$V = \frac{100 \times 30}{60} = 50 \text{ mL}$$

Mode 2: For instance, with a rate of 100 mL/hr and a volume of 50 mL, the processor 104 calculates the infusion duration as:

$$D = \frac{50 \times 60}{100} = 30 \text{ min}$$

Mode 3: For instance, with a volume of 50 mL and a duration of 30 minutes, the processor 104 calculates the infusion rate as:

$$R = \frac{50 \times 60}{30} = 100 \text{ mL/hr}$$

The infusion pump programming system 100 automatically determines the appropriate calculation mode based on the available user inputs, eliminating the need for manual selection of the calculation direction. This automated mode selection enhances user experience by simplifying the process, reducing the potential for errors, and ensuring the integrity of infusion parameters during the recalibration process.

When a user enters or modifies any two of the three parameters, the protocol generation module 112 automatically recalculates the third dependent parameter using the above relationships to maintain mathematical consistency of the infusion protocol.

In preferred embodiment, the protocol generation module 112 is configured to generate the initial infusion protocol that comprises multiple sequential steps with varying infusion rates. The infusion protocol includes one or more of the following step types an initial flush using saline or another compatible solution, one or more ramp-up steps for gradual dose escalation, a main infusion step delivered at a target rate, one or more ramp-down steps for controlled dose de-escalation, and a terminal flush step to clear the infusion line.

The protocol generation module 112 implements an automatic step-based computational logic for determining infusion parameters for each step of the protocol. When a step is designated as an "until complete" step, the protocol generation module 112 calculates the remaining infusion volume by subtracting a cumulative volume assigned to all preceding steps from the prescribed total infusion volume. The duration of the step is then derived based on the remaining volume and the specified infusion rate.

For all other steps, the protocol generation module 112 is configured to compute any missing parameter based on the two parameters provided for that step. Where the infusion rate and step duration are specified, the protocol generation module 112 determines the corresponding infusion volume for that step. Where the infusion rate and infusion volume are specified, the protocol generation module 112 determines the corresponding step duration. Where the step duration and infusion volume are specified, the protocol generation module 112 determines the corresponding infusion rate necessary to deliver the defined volume within the allotted time.

In one embodiment, the processor 104 automatically classifies infusion steps as fixed or adjustable using positional logic without requiring manual user designation. Steps at indices 0 through (n−3) are classified as fixed-parameter steps with predetermined rates and volumes that cannot be modified during calibration, typically representing pre-flush and ramp-up phases with clinically predetermined escalation profiles. Steps at indices (n−2) and (n−1) are classified as adjustable-parameter steps eligible for calibration, typically representing the main infusion and post-infusion flush phases. This positional classification generalizes to protocols of any length and ensures clinical sequencing integrity while enabling automated time budget calculation.

In one embodiment, the infusion pump programming system 100 enables a user to modify the infusion rate while preserving all originally prescribed medication volumes. The volumes of the main infusion step and the flush step are first explicitly locked, ensuring that recalibration cannot alter drug dosage. Using the fundamental relation Duration=(Volume×60)÷Rate, the infusion pump programming system 100 recalculates the durations of these steps based on the new rate. The infusion pump programming system 100 then enforces mandatory synchronization between the main infusion rate and flush rate through a single atomic assignment that updates both steps simultaneously. This prevents any temporary desynchronization and satisfies device requirements that the rates be identical. After step-level updates, the total protocol time is computed using a bottom-up aggregation of all step durations, which avoids errors from floating-point drift. The infusion pump programming system 100 performs validation checks to ensure: (i) the new rate is within allowable bounds, and (ii) the main and flush rates match within ±0.01 mL/hr. A manual edit-propagation mechanism ensures synchronization remains enforced during user input.

In one embodiment, when the user specifies a target total infusion time, the infusion pump programming system 100 computes the required infusion rate by algebraically inverting the standard infusion formula. The infusion pump programming system 100 automatically identifies fixed steps (indices 0 to n−3) and adjustable steps (indices n−2 and n−1) using positional logic. The time consumed by fixed steps is subtracted from the target total time to determine the remaining available time. If the remaining time is zero or negative, or if the resulting rate would exceed device limits, the calibration request is rejected before any changes occur. For feasible cases, the infusion pump programming system 100 applies Rate=(Volume×60)÷Duration to determine the required synchronized rate for the main and flush steps, then computes corresponding durations. A post-calculation check confirms that the recalculated durations meet the target time within a small tolerance (e.g., ±0.1 minutes).

In one embodiment, the infusion pump programming system 100 could complete all recalculation operations in a single computational pass by enforcing three constraints during computation: explicit preservation of step volumes, exact allocation of remaining time across adjustable steps, and a synchronized rate assignment for the main and flush steps. Because these constraints are satisfied during parameter construction, all validation checks pass immediately, eliminating any need for iterative refinement. This produces deterministic, O (1) recalibration suitable for safety-critical infusion pump environments. In one embodiment, O(1) means one calculation pass, without requiring iterative refinement algorithms.

In one embodiment, the protocol generation module 112 defines a special programmable step type referred to as "Until Complete." This step type enables automatic computation of the remaining infusion volume based on the total prescribed dose and the cumulative volumes of all prior steps within the same protocol. The "Until Complete" logic allows the user to define the initial steps (for example, pre-flush, ramp-up, and main infusion) and then designate the final step as "Until Complete," thereby ensuring that any remaining undelivered volume is automatically infused during that step.

The infusion pump programming system 100 determines the remaining volume $V_{UC}$ for the "Until Complete" step according to the following relationship:

$$V_{UC} = V_{Total} - \sum_{i=1}^{n-1} V_i$$

where $V_{Total}$ represents the total programmed dose for the infusion, and $V_i$ represents the delivered volume of each preceding step. The infusion pump programming system 100 dynamically recalculates $V_{UC}$ whenever a preceding step is edited or recalibrated, ensuring that total infused volume remains invariant.

The "Until Complete" step may be combined with either a constant or variable rate mode. In constant rate mode, the duration of the "Until Complete" step is computed using the relationship:

$$T_{UC} = \frac{V_{UC} \times 60}{R_{UC}}$$

In variable rate mode, the rate profile for the final step is interpolated from preceding step trends to preserve overall ramp continuity.

In one embodiment, the auto-step logic also includes automatic step classification, where the infusion pump programming system 100 identifies the role of each step within a sequence (such as ramp-up, main, ramp-down, or flush) based on its relative position and rate value. This classification allows the protocol generation module to enforce hierarchical constraints, such as $R_{ramp\text{-}up} < R_{main} < R_{ramp\text{-}down}$, and to synchronize transition steps when recalibration occurs.

This automated "Until Complete" and step-classification logic reduces the need for manual programming, prevents cumulative dosing errors, and ensures that all multi-step infusions are internally consistent with the prescribed total dose and the clinical step hierarchy. The functionality also supports recalibration integration, as changes to any prior step automatically propagate to the "Until Complete" step volume and duration.

In one embodiment, a validation module 116 verifies protocol integrity by confirming that the cumulative volume of all steps matches the prescribed infusion volume, that the total computed infusion duration aligns with the expected administration time, that infusion rate transitions between adjacent steps meet continuity constraints, and that no step exceeds predefined maximum allowable infusion rate limits for patient safety. The validation module 116 is configured to apply tolerance limits of ±0.1 mL for total volume and ±1 minute for total infusion duration. A validation status with specific error messages when the cumulative volume is mismatched with the prescribed total infusion volume is displayed on the user interface 108.

In one embodiment, the processor 104 is configured to classify the plurality of infusion steps into step types including a pre-infusion flush, one or more ramp-up steps, a main infusion step, one or more ramp-down steps, and a post-infusion flush.

In one embodiment, a calibration module 114 is configured to receive a calibration command, through the processor 104, selecting at least one of a rate calibration mode in which a new infusion rate is applied, and a time calibration mode in which a new total infusion duration is applied.

In one embodiment, the calibration module 114 is configured to receive the calibration command from a mode selector, which is configured to enable a user to select between the rate calibration mode and the time calibration mode. The mode selector is displayed on the user interface 108.

In one embodiment, the calibration module 114 is configured to recalculate the infusion parameters of the plurality of infusion steps based on the selected calibration mode while preserving at least one of total infusion volume when recalibrating time or rate, and total infusion duration when recalibrating infusion rate or volume.

In one embodiment, the calibration module 114 is configured to apply an algorithmic recalibration process, which is configured to proportionally adjust rate and duration parameters while maintaining predetermined clinical step hierarchy and safety constraints. The predetermined clinical step hierarchy among the ramp-up, main, and ramp-down steps stored in the database 124.

In the rate calibration mode, the calibration module 114 is configured to recalculate infusion durations while preserving infusion volumes. In the time calibration mode, the calibration module 114 is configured to recalculate infusion rates while preserving infusion volumes. The calibration module 114 performs deterministic bottom-up aggregation by computing total duration and total volume exclusively from individual step parameters, thereby eliminating floating-point drift.

In a preferred embodiment, the calibration module 114 enables real-time adjustment of calculated infusion parameters through selectable calibration modes. To support dynamic recalibration of infusion steps, the calibration module 114 defines a mathematical calibration core that governs the quantitative relationship between rate (R), volume (V), and duration (T). This mathematical framework enables precise computation and adjustment of infusion parameters while maintaining overall dose integrity and ensuring synchronization across multiple steps.

The foundational relationship (core equation) among these parameters is expressed as:

$$V = (R \times T)/60$$

where V represents the infusion volume in milliliters (mL), R represents the infusion rate in milliliters per hour (mL/hr), and T represents the infusion duration in minutes.

This equation serves as the governing invariant for all calculations performed by the calibration module 114.

For any recalibration event initiated by a user or by automated optimization, the calibration module 114 enforces the volume-preservation condition:

$$\Delta V = \left(R' \times \frac{T'}{60}\right) - V = 0$$

ensuring that the total infused volume remains unchanged even when either rate or duration is modified. The calibration module 114 thereby guarantees dose consistency for each infusion step and across the entire protocol.

In one embodiment, the mathematical calibration core defines two complementary recalibration modes, the rate calibration mode, and the time calibration mode.

The rate calibration mode also referred to as a forward calibration process. In the rate calibration mode, responsive to a user input specifying a revised target infusion rate, the calibration module 114 recalculates the durations of the plurality of infusion steps while maintaining the previously determined step infusion volumes. The reevaluation includes adjusting the duration of the main infusion step and any associated flushing steps based on the revised rate, and automatically determining an updated total infusion time resulting from the revised rate. When a user modifies the rate of any step, the solver recalculates the corresponding duration using the equation:

$$T' = \frac{V \times 60}{R'}$$

In the time calibration mode, responsive to a user input specifying a revised total infusion time, the calibration module 114 computes an infusion rate required to achieve the specified total time while preserving the previously determined step infusion volumes. The calibration module 114 recalculates the durations of the individual infusion steps in proportion to the revised total infusion time and applies the computed infusion rate across the main infusion step and any corresponding flushing steps to maintain protocol consistency.

In one embodiment, the calibration module 114 implements an inverse problem solver that calculates required infusion rates from target time constraints. When the user specifies a new total infusion duration, the calibration module 114 performs feasibility pre-validation before executing any calculations. The calibration module 114 automatically identifies fixed steps (indices 0 to n−3) using positional logic and calculates the time consumed by these predetermined steps. The infusion pump programming system 100 then computes the remaining time budget and performs pre-execution validation to detect mathematical impossibility when: (i) remaining time ≤0 minutes, indicating fixed steps already exceed the target time, or (ii) the required rate >999 mL/hr, exceeding device capabilities. This fail-fast approach prevents invalid system states and provides descriptive error messages before any parameter changes occur.

For feasible cases, the infusion pump programming system 100 calculates the required rate using the inverse formula: R=((V_main+V_flush)/T_remaining)×60, where V_main and V_flush represent the preserved volumes of the main and flush steps, and T_remaining represents the time available after accounting for fixed steps. This algebraic transformation of the fundamental infusion formula enables reverse calculation from time to rate, which is not implemented in conventional forward-only infusion calculators.

The time calibration mode also referred to as a reverse rate calculation process, which enables recalibration of infusion rate values when an infusion duration is modified by the user or by an automated optimization routine. The time calibration mode ensures that the total infusion volume (V) remains invariant across the recalibration operation, thereby preserving the drug dose integrity defined in the original infusion protocol.

In operation, when a user adjusts the duration of a particular infusion step, the calibration module 114 automatically computes a new infusion rate (R') corresponding to the modified duration (T') according to the following relationship:

$$R' = \frac{V \times 60}{T'}$$

where V represents the step volume (in mL), T' is the recalibrated step duration (in minutes), and R' is the resulting rate (in mL/hr). The module thereby maintains the invariant:

$$\Delta V = \left(R' \times \frac{T'}{60}\right) - V = 0$$

which ensures volume-preserving recalibration across all steps of the infusion sequence.

The time calibration mode further propagates recalibration changes through all dependent steps within the same protocol, such that sequential step durations and total infusion time remain synchronized. In embodiments including pre-flush, ramp-up, main, and ramp-down phases, the calibration module 114 enforces a clinical step hierarchy rule (e.g., $R_1 < R_2 < R_3 < R_4$), ensuring clinical consistency and smooth rate transition between successive steps.

In another embodiment, the calibration module 114 utilizes a step-type encoding table to store and manage the clinical roles of each infusion step. The encoding table assigns a unique integer identifier to each step category, including: 0=pre-infusion flush, 1=ramp-up step, 2=main infusion step, 3=ramp-down step, and 4=post-infusion flush. This encoded representation is stored within each step object and is used by the calibration module 114, the validation module 116 to ensure correct clinical ordering and to enforce type-specific recalibration constraints.

The mathematical calibration core further includes hierarchical synchronization logic that preserves clinical ordering of infusion steps. When recalibration affects one step, dependent steps are proportionally adjusted to maintain predefined sequence rules (for example, ramp-up rate<main rate<ramp-down rate). The infusion pump programming system 100 also maintains total infusion time alignment so that recalibration does not alter cumulative protocol duration beyond tolerance limits.

In embodiments where multiple steps are defined, the total infusion volume across all steps satisfies:

$$\sum_{i=1}^{n} V_i^1 = \sum_{i=1}^{n} V_i$$

Following computation, the updated rate values are verified against the validation module 116 that includes at least formula validation, total-volume validation, and duration synchronization checks. If the recalculated rate exceeds the permissible range defined in the drug protocol or device limit database, the infusion pump programming system 100 automatically applies bounded correction or issues an alert to the user interface for manual adjustment.

In one embodiment, the calibration module 114 performs the time calibration mode in a single-pass deterministic computation, avoiding iterative loops and rounding discrepancies. Floating-point precision control ensures that cumulative rounding error across all recalibrated steps remains below ±0.1 mL for the total infusion.

Through this mathematical calibration core, the infusion pump programming system 100 achieves a single-pass convergence, meaning that a valid recalibrated solution is computed deterministically without iterative back-propagation. This approach minimizes processing time and eliminates compounding errors, enabling real-time recalibration suitable for embedded or portable infusion devices. The single-pass convergence process or the single-pass convergence produces, in a single computational traversal, recalibrated rate and duration values using non-iterative closed-form equations, thereby preventing floating-point drift and eliminating intermediate unsafe states. The single-pass convergence through constraint enforcement during calculation construction. The single-pass convergence process produces, in a single computational traversal, recalibrated rate and duration values using non-iterative closed-form equations, thereby preventing floating-point drift and eliminating intermediate unsafe states. The single-pass convergence comprises computing a plurality of recalibrated rates and duration values in a single, non-iterative traversal using closed-form equations.

In one embodiment, the single-pass convergence designed to ensure deterministic alignment of rate, time, and volume parameters without iterative refinement. The single-pass convergence begins by enforcing a volume-preservation constraint, wherein all step-volume values are locked and treated as fixed inputs prior to adjustment. The calibration module 114 then enforces a time-distribution constraint, deriving updated step durations through direct mathematical computation such that the aggregate duration is preserved by construction. A further rate-synchronization constraint is applied through atomic assignments that update rate parameters in a single operation, ensuring that no intermediate or inconsistent state exists during recalculation. Because each constraint is inherently satisfied during execution, the calibration requires only the single computational pass. Following the derivation, the calibration module 114 performs a consistency validation to confirm alignment across rate, volume, and time, after which the fully validated protocol is produced without performing any iterative back-adjustment or multi-pass convergence loops.

In one embodiment, the infusion pump programming system 100 is configured to explicitly lock medication volumes before parameter adjustment, enforce time distribution exactness through mathematical derivation, and apply rate synchronization through an atomic assignment. All validation criteria are satisfied by construction during the single computational pass without requiring iterative refinement. The calibration module 114 performs an atomic assignment that simultaneously writes the same infusion rate value to both the main infusion step and the flush step.

In one embodiment, the calibration module 114 implements a bidirectional calibration solver configured to perform both forward calibration (rate-to-duration adjustment) and reverse calibration (duration-to-rate adjustment) in a unified computational framework. The solver enables the infusion pump programming system 100 to automatically respond to any change in a dependent infusion parameter while maintaining the total programmed volume as an invariant quantity.

The bidirectional solver continuously evaluates all steps within an infusion protocol and propagates parameter changes in real time. When a user modifies the rate of any step, the solver recalculates the corresponding duration. Conversely, when the duration of a step is modified, the solver recalculates the rate. These two complementary operations ensure that the total infused volume V remains constant for each step and for the entire protocol.

The bidirectional solver is integrated with an internal rate synchronization engine, which aligns recalibration effects across related infusion steps. For example, when a main infusion step is recalibrated, the infusion pump programming system 100 proportionally adjusts associated pre-flush, ramp-up, and ramp-down steps to preserve their clinical hierarchy. As used herein, the clinical hierarchy means the predetermined order: pre-flush→ramp-up→main→ramp-down→post-flush. The synchronization engine enforces relational constraints such as:

$$R_{ramp-up} < R_{main} < R_{ramp-down}$$

and ensures that transitions between steps maintain smooth rate gradients and consistent total duration.

In one embodiment, the rate synchronization engine applies a weighted propagation algorithm that distributes recalibration effects based on relative step duration or rate magnitude. This ensures that the adjustment of one step does not create abrupt transitions or violate total time constraints. The recalibrated step set is then validated through the six-layer validation framework, confirming formula consistency, total volume accuracy, and device compliance.

The bidirectional calibration solver operates as a single-pass deterministic algorithm, meaning that each recalibration event produces a converged and validated parameter set without requiring iterative correction. This improves computational efficiency and allows real-time recalibration suitable for embedded infusion control systems.

Together, the bidirectional calibration solver and rate synchronization engine establish a robust mathematical foundation for dynamic protocol adjustment, guaranteeing that any recalibration whether forward or reverse, preserves both the quantitative volume invariants and the qualitative clinical logic of the infusion sequence.

In one embodiment, the rate synchronization engine is configured to maintain deterministic alignment between the main infusion rate and the flush rate. The rate synchronization engine utilizes an atomic assignment operation in which both rate parameters are updated simultaneously, thereby preventing the existence of any transient or intermediate state in which the two rates differ. As used herein, the atomic assignment means the simultaneous update of two parameters such that no intermediate values exist in system memory.

During recalibration, the rate synchronization engine applies the updated rate value to both parameters in a single indivisible operation and subsequently performs a validation check to confirm that the absolute difference between the synchronized rates satisfies the tolerance condition |R_main−R_flush|≤0.01 mL/hr. If the validation fails, the infusion pump programming system 100 rejects the recalibration and issues an alert to the user. Furthermore, when the user manually modifies the main infusion rate, the infusion pump programming system 100 automatically propagates the new value to the flush rate, ensuring continuous rate synchronization throughout all user interactions.

This bidirectional calibration capability, which includes both forward calibration (rate-to-duration) and reverse calibration (duration-to-rate), enables dynamic and reliable adjustment of infusion programs while ensuring the total infused volume remains constant. The result is a clinically compliant, volume-preserving recalibration framework that allows modification of infusion parameters without compromising dose accuracy or step synchronization. The recalibrated parameters are then processed by the validation module 116 to confirm mathematical consistency, clinical feasibility, and compliance with the stored infusion safety limits.

The above framework forms the computational basis for all subsequent calibration and validation operations performed by the calibration module 114, ensuring that every recalibrated parameter set remains mathematically consistent and clinically safe.

The infusion pump programming system 100 incorporates a volume preservation proof and error minimization framework to ensure that all recalibration operations maintain the total programmed infusion volume invariant within defined clinical tolerances. The framework mathematically verifies that the sum of all recalculated step volumes equals the originally prescribed total volume, regardless of rate or duration modifications.

For any infusion step i, the recalculated volume $V_i'$ is expressed as:

$$V_i' = \frac{R_i' \times T_i'}{60}$$

where $R_i'$ and $T_i'$ are the recalibrated rate (mL/hr) and duration (minutes), respectively. The infusion pump programming system 100 enforces the invariant:

$$\sum_{i=1}^{n} V_i' = \sum_{i=1}^{n} V_i$$

ensuring that cumulative dose delivery remains unchanged even when one or more parameters are modified.

To validate this property, the infusion pump programming system 100 performs a post-recalibration volume verification pass, comparing the cumulative recalculated total $\Sigma V_i'$ with the target programmed volume $V_{Total}$. Any deviation beyond the permissible tolerance (±0.1 mL or ±0.05% of the total programmed dose, whichever is greater) triggers automatic corrective rounding or proportional adjustment across all steps to restore total-volume invariance.

In one embodiment, the infusion pump programming system 100 minimizes residual rounding or arithmetic drift through a distributed error compensation algorithm, which adjusts the final step volume or duration by the computed residual difference:

$$\epsilon = V_{Total} - \sum_{i=1}^{n} V_i'$$

The algorithm redistributes this residual $\in$ either to the "Until Complete" step or to the last active step in the protocol, ensuring that cumulative delivery matches the prescribed total volume precisely.

This error minimization approach prevents the accumulation of floating-point discrepancies, especially in multi-step infusions with small individual volumes or complex ramp profiles. When used in combination with the floating-point precision control framework, the infusion pump programming system 100 maintains total volume deviations below ±0.1 mL even after multiple recalibration cycles.

In one embodiment, the infusion pump programming system 100 employs a bottom-up aggregation framework to ensure numerical accuracy of cumulative infusion parameters such as total duration, total volume, or total delivered medication. Under this framework, individual step parameters serve as the authoritative source of truth, and all aggregate values are derived exclusively from these individual entries rather than being maintained as independent variables. This approach prevents cumulative drift, synchronization errors, and discrepancies arising from floating-point rounding behavior.

During operation, the infusion pump programming system 100 recalculates aggregate duration by iterating through all infusion steps and computing a fresh summation of each step's duration. Because the aggregate is always derived from the exact underlying components, the infusion pump programming system 100 avoids accumulation of rounding errors that may occur when aggregates are incrementally updated. This ensures that the displayed total duration, total volume, or total rate-adjusted time remains mathematically consistent with the individual step values.

In this mechanism, each step's duration parameter is considered the authoritative value. The infusion pump programming system 100 computes the total infusion duration by summing the duration of all steps. No separate aggregate-duration variable is maintained, and the infusion pump programming system 100 never updates the total by incremental adjustments. Instead, the aggregate value is reconstructed each time it is requested or modified. This guarantees that inconsistencies-such as drift caused by repeated incremental calculations, floating-point artifacts, or inconsistent back-propagation-cannot arise.

The bottom-up approach ensures that aggregate parameters are always derivative, never primary. As a result, individual step durations remain the single source of truth, the aggregate total is always mathematically fresh, and no desynchronization occurs between displayed totals and underlying step values. This method significantly reduces floating-point deviation over long sequences of step adjustments.

In another embodiment, the infusion pump programming system 100 implements a compensation adjustment mechanism designed to normalize decimal irregularities that arise during infusion-volume calculations. Certain decimal values are considered non-conforming for specific clinical devices (e.g., values such as x.1 to x.4 or x.6 to x.9). When a computed volume falls into these non-conforming ranges, the infusion pump programming system 100 automatically adjusts the value to the closest acceptable standardized increment (for example, rounding to a whole value or to a half-unit value).

Once an adjusted volume is determined, the infusion pump programming system 100 computes the volume difference between the originally calculated volume and the normalized volume. This difference is then assigned to a designated compensation step, ensuring that total volume consistency is maintained across the entire infusion profile. The compensation step's duration is automatically recalculated based on its rate and the adjusted volume. This technique ensures that device-imposed rounding constraints do not compromise overall dosage accuracy. This section describes the general design principle governing all aggregate calculations within the infusion pump programming system 100. The core guideline is that individual step parameters are always authoritative, and aggregate values must never be maintained independently or updated incrementally. Instead, the infusion pump programming system 100 continuously recalculates aggregates using a full evaluation of all individual step values.

This architectural rule prevents the introduction of floating-point drift, ensures consistency after user edits, and avoids error accumulation during multi-step infusion programming. By deriving totals exclusively from underlying components, the infusion pump programming system 100 guarantees deterministic and repeatable results, even when users adjust steps in nonlinear or iterative workflows.

Through this mathematically verified proof of volume preservation and active error minimization, the infusion pump programming system 100 ensures deterministic compliance between programmed and delivered dose quantities, thereby achieving the computational accuracy required for clinical-grade infusion programming.

For clarity of description and reproducibility, the infusion pump programming system 100 defines the following mathematical notation used throughout the calibration and validation processes:

TABLE 1

| Symbol | Definition | Units |
|---|---|---|
| $V_i$ | Volume of step i before recalibration | mL |
| $V'_i$ | Volume of step i after recalibration | mL |
| $R_i$ | Infusion rate of step i before recalibration | mL/hr |
| $R'_i$ | Recalculated rate of step i | mL/hr |
| $T_i$ | Duration of step i before recalibration | min |
| $T'_i$ | Recalculated duration of step i | min |
| n | Total number of steps in the infusion protocol | — |
| $V_{Total}$ | Total programmed infusion volume | mL |
| $\in$ | Residual volume error after recalibration | mL |
| $\Delta V$ | Volume deviation between recalculated and reference total | mL |
| $\tau$ | Validation tolerance threshold | — |

In one embodiment, the processor 104 is configured to execute the validation module 116 to validate the recalibrated infusion protocol for clinical safety and mathematical consistency prior to execution. The validation module 116 provides visual indicators that comprise a green check for valid parameters and a red warning symbol for invalid parameters.

In one embodiment, the validation module 116 implements a six-layer validation architecture designed to ensure that every recalibrated infusion protocol satisfies mathematical accuracy, clinical safety, and device-specific compliance before execution or documentation. Each validation layer operates in a defined order, with any failure at a lower layer preventing subsequent calculations or display. The validation layers are input validation layer, feasibility validation layer, synchronization validation layer, formula validation layer, volume validation layer, and duration validation layer.

The input validation layer verifies that all entered infusion parameters, rate, duration, and volume are numerically valid, within accepted clinical ranges, and correspond to recognized drug or device units. The feasibility validation layer ensures that calculated parameters are physically and clinically achievable, confirming that rates do not exceed pump limits and durations meet minimum step thresholds.

The synchronization validation layer checks sequential and relational constraints between adjacent steps, including ramp-up/ramp-down ordering and flush synchronization. The formula validation layer confirms mathematical coherence between rate, duration, and volume using the core equation and validates recalibrated results from both Forward and Reverse Calibration modes.

The volume validation layer verifies that the cumulative programmed volume equals the prescribed dose, enforcing a total-volume tolerance of +0.1 mL. The duration validation layer validates that the total infusion duration, as recalculated, matches the user-defined or protocol-specified total time within +0.5% tolerance.

The six-layer validation architecture operates in real time during both user interaction and automated recalibration. Each validation pass generates structured output data comprising pass/fail flags and corrective recommendations, which are communicated to the user interface and to a document generation module 120.

To maintain computational precision, the validation framework employs hierarchical tolerance management, wherein early layers apply strict absolute tolerances while later layers use proportional or cumulative tolerances to prevent error propagation. All computations use controlled floating-point rounding to maintain consistent totals across sequential steps, ensuring that cumulative rounding error remains within ±0.1 mL per protocol.

This layered approach allows deterministic identification of parameter inconsistencies at the earliest stage, minimizes recalculation loops, and ensures that any validated protocol conforms simultaneously to mathematical, clinical, and device constraints.

In one embodiment, the hierarchical tolerance model designed to provide robust validation of infusion parameters while preventing the propagation of cumulative numerical error. The model applies a comparatively broader tolerance of ±0.5 mL at the individual-step level, reflecting standard syringe graduation precision, while enforcing a significantly tighter ±0.1 mL tolerance at the aggregate total-volume level to ensure that step-level deviations cancel rather than accumulate. A further tolerance of ±0.01 mL/hr is applied to rate-synchronization validation, consistent with floating-point numerical precision limits, and an additional ±1-minute tolerance is applied to aggregate total-duration validation to account for pump display resolution and clinical acceptability thresholds. Collectively, these graduated tolerances create a multi-level validation structure that is non-obvious over uniform tolerance approaches, as it strategically balances measurement usability with clinical safety and mathematically compels rounding discrepancies to offset one another rather than compound.

TABLE 2

| Validation Level | Parameter | Tolerance | Justification |
|---|---|---|---|
| Formula validation layer | Volume | ±0.5 mL | USP syringe graduation standard |
| Volume validation layer | Total Volume | ±0.1 mL | Prevents cumulative error (5 × 0.5 = 2.5 mL max) |
| Synchronization validation layer | Rate Sync | ±0.01 mL/hr | IEEE 754 floating-point precision limit |
| Duration validation layer | Total Duration | ±1 minute | Pump display resolution; clinical threshold |

In one embodiment, the infusion pump programming system 100 incorporates a floating-point rounding and precision control mechanism to minimize numerical inconsistencies during recalibration and validation computations. Because infusion rate, duration, and volume are interdependent parameters derived through multiple floating-point operations, rounding discrepancies can accumulate over successive steps and cause measurable deviations in total infusion volume or duration. The precision control mechanism prevents such deviations and ensures deterministic output across all computing environments.

The rounding and precision control mechanism enforces a consistent arithmetic precision policy across all modules, including the protocol generation, calibration, and validation modules. Each computational step applies a controlled rounding operation to three decimal places for intermediate values and two decimal places for displayed values, using a deterministic "round half to even" rule to prevent statistical bias.

In one embodiment, the infusion pump programming system 100 introduces guard digits during internal rate and duration calculations, extending the precision by at least two additional significant digits before the final rounding operation. This minimizes propagation of truncation error, especially when recalibration involves small-volume or short-duration steps.

To maintain total-volume consistency across multi-step infusions, the infusion pump programming system 100 performs cumulative precision verification according to:

$$\left|\sum_{i=1}^{n} V_i' - \sum_{i=1}^{n} V_i\right| \leq 0.1 \text{ mL}$$

where $$V_i'$$

and $V_i$ denote recalculated and original step volumes, respectively. If the cumulative deviation exceeds this tolerance, the infusion pump programming system 100 automatically reapplies constrained rounding or correction to restore the invariant.

The precision control framework also ensures cross-platform determinism, meaning that recalculated results remain identical regardless of computing hardware, software version, or operating environment. This capability enables consistent outcomes when infusion programs are generated, verified, or transferred between systems such as hospital pharmacy software, embedded pump firmware, or mobile verification tools.

Through this floating-point rounding and precision control mechanism, the infusion pump programming system 100 maintains reliable numerical integrity while preserving clinical accuracy and ensuring that all recalculated protocols satisfy the prescribed total volume and duration tolerances.

In one embodiment, the processor 104 is configured to execute the document generation module 120 to generate an infusion output that includes patient information, infusion parameters, and a graphical code. The document generation module 120 generates a document containing a QR code encoding infusion parameters in a structured data format. The graphical code encodes a structured data payload comprising a JSON or XML representation of the plurality of infusion steps for the recalibrated protocol. In one embodiment, the document generation module 120 provides an exportable document containing the multi-step infusion protocol with patient information and infusion parameters.

In a preferred embodiment, the document generation module 120 is configured to assemble a structured programming document comprising multiple sections, including but not limited to, patient information section, medication details section, infusion parameter section, machine-readable code integration, and verification and traceability section.

In one embodiment, the document-generation module 120 encodes the final infusion protocol into a structured payload schema prior to generating the graphical code (QR code). The payload includes fields such as protocol identifier, patient ID hash, step number, encoded step type, infusion rate, duration, volume, and a protocol version number. Each field is serialized into a compact binary format that ensures consistent interpretation by downstream clinical systems.

A QR generation engine supports error-correction levels, enabling recovery from up to 30% data loss. This ensures that even partially damaged or low-resolution QR images remain decodable by clinical scanners, preserving medication safety and workflow reliability.

In the patient information section, the processor 104 is configured to retrieve and populate patient-specific information fields, including patient name, date of birth, medical record number, encounter or account number, and a prescription or order identifier associated with the infusion. The patient information section may further include optional parameters such as patient weight, diagnosis, allergy alerts, or physician details to support clinical review and compliance requirements.

In the medication details section, the processor 104 is configured to insert medication-related data including the drug name, concentration or strength, dosing instructions, preparation or compounding details, vial or container configurations used for preparation, and expiration or beyond-use dating information. The document generation module 120 may further list lot numbers, manufacturer or supplier details, and storage or handling precautions for traceability.

The document generation module 120 is configured to automatically populate infusion programming parameters derived from the protocol generation module 112, including total prepared volume with priming and flushing allowances, total infusion time and target infusion rate, and a detailed multi-step infusion protocol specifying, for each step, at least the step type, infusion rate, duration, and delivered volume. In some embodiments, safety-related annotations, rate change warnings, or required monitoring instructions are appended to the infusion parameter section.

The document generation module 120 is configured to encode selected infusion parameters and metadata into a graphical code, such as a QR code, Data Matrix code, or barcode. Encoded data may include patient identifiers, medication identifiers, protocol parameters, timestamps, document version numbers, and a cryptographic or digital signature to verify authenticity and detect tampering. The processor 104 is further configured to embed the machine-readable code within the generated document for subsequent scanning by an infusion pump, mobile application, or electronic medical record (EMR) system.

The document generation module 120 is configured to incorporate a verification block including fields for recording personnel authentication and quality assurance. The verification and traceability section may include signatures, initials, or digital credentials of, the clinician or operator who generated the programming sheet, the individual who entered the program into the pump, and an independent checker validating the programming accuracy. Additional traceability elements may include pump or device identifiers, software or firmware version numbers, calibration or maintenance due dates, and audit tracking codes.

In one embodiment, the execution of the document generation module 120 causes the processor 104 to perform a document generation workflow comprising data acquisition, data encoding, document assembly, code embedding, file generation and identification, and export and distribution. First, aggregating input parameters, calculated infusion values, and protocol details from the dose evaluation module 110, the calibration module 114, and a dose safety validation module 128, optionally including user-entered notes or overrides. Then, generating an encoded payload of selected data attributes, converting the payload into the graphical code, and storing a corresponding digital record for audit synchronization. Next, constructing a structured document template and inserting the populated data into predefined sections, including formatted tables, headers, footers, and clinical reference fields. Next, embedding the graphical code into the document at a designated location for scan-based retrieval and automated pump programming. Then, generating a digital or printable document file, assigning a unique filename incorporating patient or medication identifiers, timestamps, and versioning metadata for archival and traceability. Later, delivering the document to a user interface for preview, printing, storage, or secure transmission to a pump, EMR system, pharmacy system, or clinical workstation.

In one embodiment, the infusion pump programming system 100 comprises a vial optimization module 118, which is configured to receiving a required dose value for a selected medication, retrieving available vial sizes including strength values from the database 124. The vial optimization module 118 is configured to generate a plurality of vial combinations up to a predefined maximum vial count, calculate, for each vial combination, total drug amount, waste amount, and waste percentage, and rank the vial combinations based on minimum waste percentage, and further display an optimal vial combination to a user based on the ranking through the user interface 108.

In a preferred embodiment, the vial optimization module 118 is configured to execute a dynamic programming model to generate the plurality of vial combinations up to a predefined maximum vial count. The dynamic programming model excludes vial combinations having waste percentage above a predefined threshold. The user interface 108 permits manual override of the optimal vial combination. The manual override features include increment and decrement controls for each vial size, round-up and round-down controls for adjusting quantities to full vials, and a real-time waste display that shows the expected wastage volume and percentage as vial quantities are changed.

In one embodiment, the vial optimization module 118 is configured to determine optimal vial combinations for medication preparation with reduced waste. The vial optimization module 118 employs the dynamic programming model that evaluates all feasible combinations of available vial sizes for a selected medication and computes corresponding waste metrics. The optimization criteria include minimizing the total unused drug amount, reducing the waste percentage relative to the total quantity of drug available in the selected vials, minimizing the number of vials required to meet the prescribed dose, and preferentially selecting combinations utilizing larger vial sizes when waste values are equivalent.

In another embodiment, the vial optimization module 118 may further provide a selectable interface enabling a user to modify or manually specify container quantities, with automatic reevaluation of drug availability, coverage of the required dose, and remaining unused quantity in response to such user input.

The vial optimization module 118 generates vial combinations by iterating through each available vial size and through a defined vial quantity range, and for each candidate combination calculating the total drug amount, the unused drug quantity, and the waste percentage. Combinations satisfying predefined waste thresholds are stored and ranked for recommendation to the user.

Additionally, the infusion pump programming system 100 provides a manual override interface that allows a healthcare provider to directly specify vial quantities. The vial optimization module 118 performs real-time reevaluation of total drug provided, patient dose coverage, and waste metrics for the manually selected configuration.

In one embodiment, the database 124 stores multiple vial sizes for each medication. A waste calculator (not shown) evaluates all possible vial combinations using a dynamic programming algorithm that ranks the vial combinations based on waste percentage and cost, and automatically selects the combination yielding minimum wastage below a predetermined threshold.

In another embodiment, the vial optimization module 118 is configured to identify one or more vial selection options that satisfy a prescribed drug requirement with reduced material waste. The vial optimization module 118 is operable to evaluate combinations of available vial configurations using an optimization technique, which may include dynamic programming, heuristic-based evaluation, or other computational search strategies. The vial optimization module 118 may determine, based on one or more optimization criteria, a preferred combination of vial quantities. The optimization criteria may include, individually or in combination, minimizing unused drug quantity, minimizing waste proportional to the total drug supplied, minimizing the number of containers required, and prioritizing vial options according to predefined selection rules when multiple combinations yield similar waste outcomes. The vial preparation assistance module 118 constrains vial selection to combinations that satisfy pump-device requirements for minimum measurable volume, minimum programmable rate, infusion-time tolerances, and drug-stability duration, thereby producing only clinically usable and pump-compatible vial configurations.

In a preferred embodiment, the vial optimization module 118 implements a multi-strategy dynamic optimization engine that generates and evaluates vial combinations using four parallel optimization strategies: minimize-vial-count strategy that prioritizes larger vials to reduce handling burden, minimize-waste strategy that prefers smaller vials for precision dosing; balanced-mix strategy that uses large vials for bulk and small vials for remainder, and exhaustive-combination-search strategy that generates multiple starting-point combinations. The infusion pump programming system 100 then ranks all generated combinations using dual-criteria global optimization, primarily sorting by waste amount in ascending order and secondarily by vial count as a tiebreaker. The optimization incorporates supply-period integration by calculating total drug requirements across the entire treatment duration using the formula: total Drug Needed=single Dose×ceil (days Supply/dose Frequency), and validates coverage using days Covered=floor (total Drug Available/daily Dose). The infusion pump programming system 100 employs intelligent thresholds that trigger alternative suggestions when waste percentage exceeds 20% or dose accuracy falls outside the 95-105% optimal range, and uses precision remainder detection with a 0.01 threshold to distinguish clinically significant remainders requiring additional vials.

In one embodiment, the dose safety validation module 128 configured to evaluate infusion dosing safety and provide real-time visual feedback. The dose safety validation module 128 maintains therapeutic dosing reference ranges for each medication, the ranges being defined per clinical indication and patient population, including specialized ranges for pediatric and geriatric patients. The dose safety validation module 128 computes a safety ratio according to:

$$\text{Safety Ratio} = \text{Calculated Dose} \div \text{Maximum Safe Dose}$$

Based on the computed safety ratio, the infusion pump programming system 100 classifies the dose into one of the following categories as shown in table 3:

TABLE 3

| Dose | Ratio |
|---|---|
| Underdosed | Safety Ratio < 0.5 |
| Sub-therapeutic | 0.5 ≤ Safety Ratio < 0.8 |
| Therapeutic | 0.8 ≤ Safety Ratio ≤ 1.0 |
| Supra-therapeutic | 1.0 < Safety Ratio ≤ 1.2 |
| Overdosed | Safety Ratio > 1.2 |

The user interface 108 displays the safety status using a semi-circular gauge incorporating a color-coded gradient transitioning from blue (underdosed) through green (therapeutic) to red (overdosed). An animated pointer or needle is positioned on the gauge according to the safety ratio, and the display is updated in real time as dosing or infusion parameters change. The user interface 108 further presents a numerical representation of the safety ratio or safety percentage.

In another embodiment, the dose safety validation module 128 is configured to assess the safety of a calculated medication dose and to provide a real-time visual or graphical representation of the safety status. The dose safety validation module 128 may reference one or more therapeutic or recommended dosing ranges associated with a medication, indication, patient category, or other clinical factors. The dose safety validation module 128 determines a safety indicator based on a comparison between the calculated dose and one or more safety thresholds, and classifies the dosing level into one of a plurality of safety categories.

The user interface 108 further provides a graphical feedback mechanism that visually communicates the safety classification, which may include a color-coded or gradient-based representation, a positional indicator on a graphical scale, and/or numerical or textual safety information. The safety indicator may update dynamically in response to changes in dose-related input parameters.

In some embodiments, the protocol generation module 112 comprises a machine learning model trained on infusion protocol datasets. The machine learning model is configured to predict safe infusion parameter ranges based on historical dosing and safety data, identify anomalies in calculated infusion parameters indicating potential overdose or unsafe infusion rates, recommend alternative infusion parameters to improve safety or efficiency. The machine learning model updates a safety model based on real-world user feedback and protocol outcomes.

In some embodiments, the machine learning model is configured to detect outlier infusion settings based on cluster-based anomaly detection. The machine learning model is configured to recommend infusion parameter adjustments that reduce risk of adverse reactions.

In some embodiment, a training dataset comprises historical infusion records, medication types, vial sizes, and patient-specific dosing outcomes. A neural network is configured to learn correlations between prescribed infusion parameters and dose safety outcomes. The neural network comprises a convolutional or transformer-based model trained to detect deviations from therapeutic dosing ranges. An AI inference engine is configured to predict optimal infusion step parameters and detect unsafe infusion combinations in real time. A feedback loop is configured to adjust dose limits based on accumulated clinical data. The feedback loop incorporates user-validated outcomes to continuously refine dosing predictions. An alert module is configured to automatically flag predicted unsafe configurations and suggest corrected infusion rates or durations prior to infusion initiation.

In one embodiment, the infusion pump programming system 100 comprises a one-click execution controller configured, responsive to a single user action, to concurrently perform the reevaluation across the plurality of infusion steps, synchronize calibrated rates across the main infusion and flush steps, and validate volume invariance, without further user input.

In a preferred embodiment, the one-click execution controller is configured to execute calibration computations and update all infusion step parameters through a single user-initiated action. The single user-initiated action is performed by the user entering a new rate value in the rate input field and activating a single calibrate control in the rate calibration mode, or by entering a new total infusion time value in the time input field and activating a single calibrate control in the time calibration mode.

When the single user-initiated action is received, the infusion pump programming system 100 automatically and simultaneously performs all required calibration operations. These operations include recalculating the durations of all infusion steps when the infusion pump programming system 100 is operating in the rate calibration mode, or recalculating the required infusion rates when the infusion pump programming system 100 is operating in the time calibration mode. the recalculating maintains a predetermined clinical step hierarchy among the ramp-up, main, and ramp-down steps stored in the database 124. The infusion pump programming system 100 also updates the total infusion time or the required infusion rate according to the selected mode. In addition, the infusion pump programming system 100 synchronizes rate changes across all relevant step types, and validates that the total infusion volume remains constant throughout the recalibrated protocol. All of these operations are completed automatically without any further user inputs, confirmation steps, or intermediate interactions between initiation and completion of the calibration process.

In one embodiment, the infusion pump programming system 100 enforces rate synchronization between the main infusion step and the post-infusion flush step using a triple-enforcement mechanism. During recalibration, the infusion pump programming system 100 performs an atomic assignment in which both the main and flush step rates are simultaneously updated to the same value, ensuring that the two steps cannot diverge. After recalculation, a synchronization validation layer confirms that the rates remain equal within ±0.01 mL/hr, accounting for floating-point precision limits. Additionally, when the user manually edits the rate of the main infusion step, the infusion pump programming system 100 automatically propagates the updated rate to the flush step to prevent desynchronization. This multi-layer enforcement mechanism ensures device compatibility, particularly for pumps that require identical rates for medication clearing, and enhances clinical dose safety.

In one embodiment, the infusion pump programming system 100 computes total infusion time and total infused volume using a bottom-up aggregation method in which the sum of all step durations or volumes is treated as the source of truth. Instead of maintaining separate running totals that may drift due to floating-point rounding, the infusion pump programming system 100 recalculates aggregate values directly from the individual step parameters after each recalibration operation. This bottom-up approach eliminates the accumulation of rounding errors, ensures internal numerical consistency, and maintains alignment between step-level values and overall protocol totals.

In one embodiment, the infusion pump programming system 100 achieves the single-pass convergence through constraint enforcement during calculation construction rather than iterative refinement. As used herein, the single-pass convergence means a recalibration algorithm that performs a complete rate-duration adjustment of all affected steps in one computational pass without iterative back-propagation, where each step's duration or rate is computed from closed-form equations.

In one embodiment, the infusion pump programming system 100 enforces three fundamental constraints during a single-pass recalibration. First, explicit volume preservation where medication volumes are locked before any parameter adjustment. Step volumes are locked as invariant. Second, time distribution exactness through mathematical derivation ensuring durations sum precisely to remaining time. The recalculated step durations or rates are generated from non-iterative closed-form equations. Third, rate synchronization through atomic assignment of identical values to main and flush steps. The processor 104 performs atomic rate synchronization by simultaneously assigning an identical recalibrated rate to both the main infusion step and the post-flush step.

These constraints, when satisfied during parameter construction, guarantee that all validation checks pass on the first attempt without requiring iterative refinement loops, resulting in O(1) computational complexity.

The single-pass convergence is mathematically proven through constraint satisfaction: volume conservation is enforced by explicit locking (ΣV_i'=ΣV_i), time distribution exactness is achieved through algebraic derivation (D_m+D_f=T_r), and rate synchronization is enforced by atomic assignment (R_flush:=R_main). Since all validation criteria are satisfied by construction, the infusion pump programming system 100 produces valid, constraint-satisfying results in exactly one computational pass, eliminating the need for iterative solvers such as Newton-Raphson or gradient descent methods.

In one embodiment, the infusion pump programming system 100 implements bottom-up aggregation where all aggregate values are derived from individual step parameters as source of truth, rather than maintaining separate running totals. The total infusion time is calculated as the sum of all step durations, and the total infusion volume is calculated as the sum of all step volumes, preventing floating-point drift that can occur when maintaining separate aggregate variables that are incrementally updated.

In one embodiment, the infusion pump programming system 100 includes Curlin pump compatibility algorithms that automatically adjust decimal volumes to end in 0.0 or 0.5 as required by specific infusion pump devices. In one embodiment, the calibration module 114 performs device-compatibility rounding of step volumes to 0.0 or 0.5 increments and redistributes the resulting volume difference to a designated compensation step while maintaining total-volume invariance. The infusion pump programming system 100 detects non-conforming decimals and applies rounding rules: decimals 0.1-0.4 round to 0.0, decimals 0.6-0.9 round to 0.5, with compensation redistribution of volume differences to previous steps to maintain total volume conservation while achieving device compliance.

Figure 2:
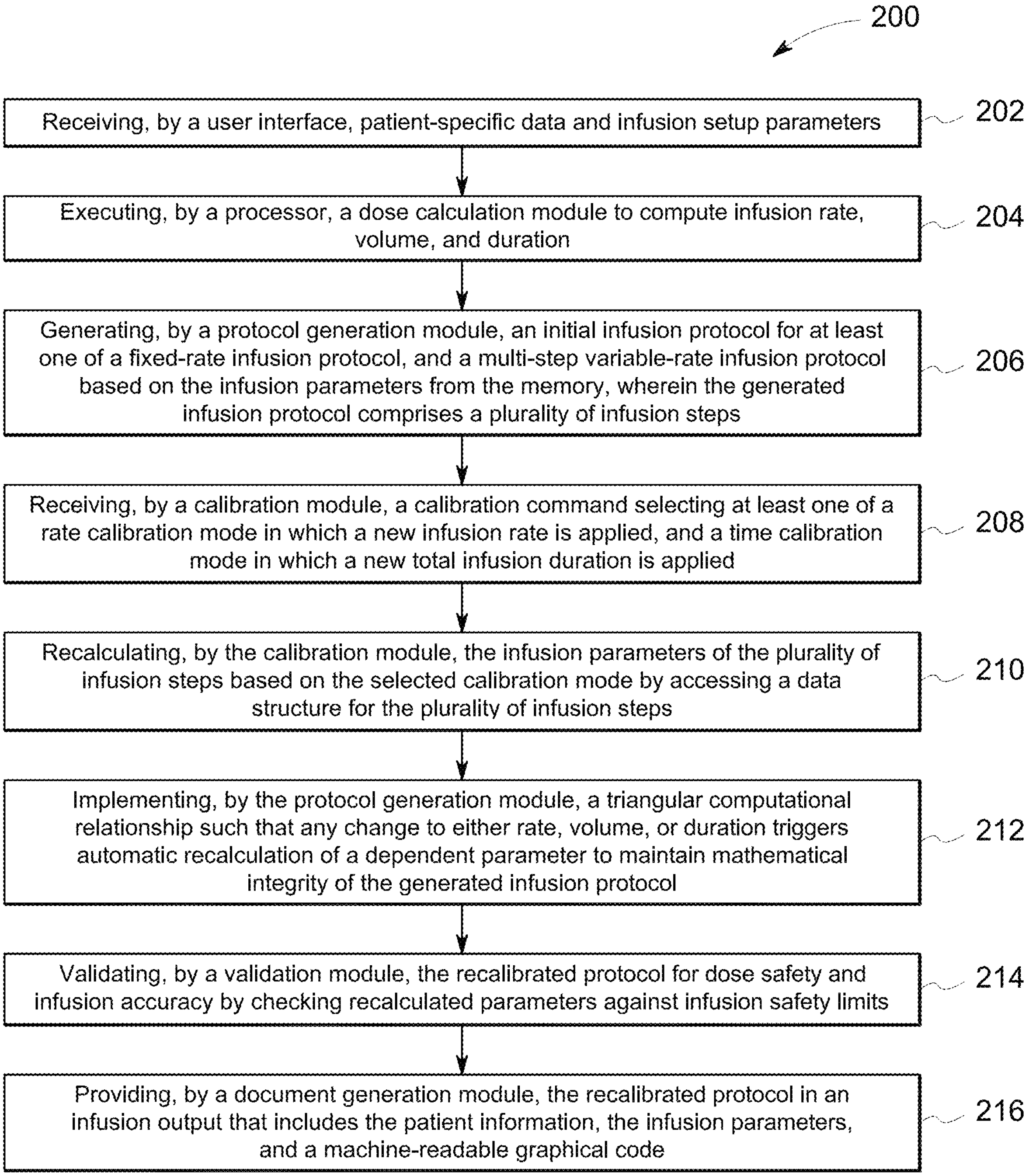
FIG. 2 illustrates a flowchart of a method for recalibrating multi-step infusion protocols using the infusion pump programming system, in accordance with embodiments of the invention.

FIG. 2 refers to a flowchart 200 of a method for recalibrating multi-step infusion protocols using the infusion pump programming system 100. At step 202, the patient-specific data and infusion setup parameters are received by the processor 104 through the user interface 108. At step 204, the dose evaluation module 110 is executed by the processor 104 to compute infusion rate, volume, and duration. At step 206, the initial infusion protocol with a plurality of steps classified by type is generated by the protocol generation module 112. The initial infusion protocol for at least one of a fixed-rate infusion protocol, and a multi-step variable-rate infusion protocol based on the infusion parameters from the memory. The generated infusion protocol comprises a plurality of infusion steps.

At step 208, a calibration command is received by the calibration module 114 to change at least one of the rate calibration mode, and the time calibration mode. At step 210, recalibration is performed within the computing device 102 to modify only non-locked steps while preserving step order, clinical logic, clinical step hierarchy, and minimum step durations. The calibration module 114 recalculates the infusion parameters of the plurality of infusion steps based on the selected calibration mode by accessing a data structure for the plurality of infusion steps.

In a preferred embodiment, the processor 104 is configured to perform reevaluation of multi-step infusion parameters by automatically adjusting either the step durations while maintaining the originally defined step volumes constant when a change to either the infusion rate is received, or the step rates while maintaining the step volumes constant when a change to the total infusion duration is received. The reevaluation is carried out such that the predefined sequential order of steps is preserved, along with the clinical logic governing clinical step hierarchy between different step types, and compliance with minimum step duration requirements obtained from the database 124.

In one embodiment, the infusion pump programming system 100 is configured to enable dynamic insertion of additional infusion steps, and upon adding a new step. The processor 104 automatically assigns a sequential step number, allocates default parameter values for rate, volume, and duration based on step type, and recalculates overall protocol sequencing to maintain correct clinical order.

Ats step 212, the triangular computational relationship is implemented by the protocol generation module 112 such that any change to either rate, volume, or duration triggers automatic reevaluation of a dependent parameter to maintain mathematical integrity of the generated infusion protocol.

At step 214, the recalibrated protocol is validated for dose safety and infusion accuracy by the validation module 116 by checking recalculated parameters against infusion safety limits.

In some embodiments herein, the validation module 116 performs structural integrity verification, which ensures that the recalibrated protocol retains the minimum required set of step types. The validation includes checks confirming that at least one ramp-up step and one ramp-down step remain present in the final sequential ordering. If removal or modification of steps results in a structure lacking either ramp class, the validation module 116 issues a structural-integrity error message and prevents protocol finalization.

In one embodiment, the validation module 116 implements a hierarchical tolerance model that applies different tolerance thresholds at different validation levels to prevent cumulative error accumulation. The infusion pump programming system 100 applies a per-step tolerance of ±0.5 mL for individual step formula validation, corresponding to USP syringe graduation standards, while enforcing a tighter aggregate tolerance of ±0.1 mL for total volume validation across all steps. This hierarchical approach forces rounding errors to cancel rather than accumulate, as the tighter aggregate tolerance prevents the theoretical maximum cumulative error of 2.5 mL (5 steps×0.5 mL) that would occur with uniform tolerances. Additional hierarchical tolerances include ±0.01 mL/hr for rate synchronization validation (IEEE 754 precision limit) and ±1 minute for total duration validation (clinical decision-making resolution).

At step 216, the recalibrated protocol is provided in an electronic format suitable for programming an infusion pump. The recalibrated protocol is provided in an infusion output that includes the patient information, the infusion parameters, and a graphical code.

Figure 3:
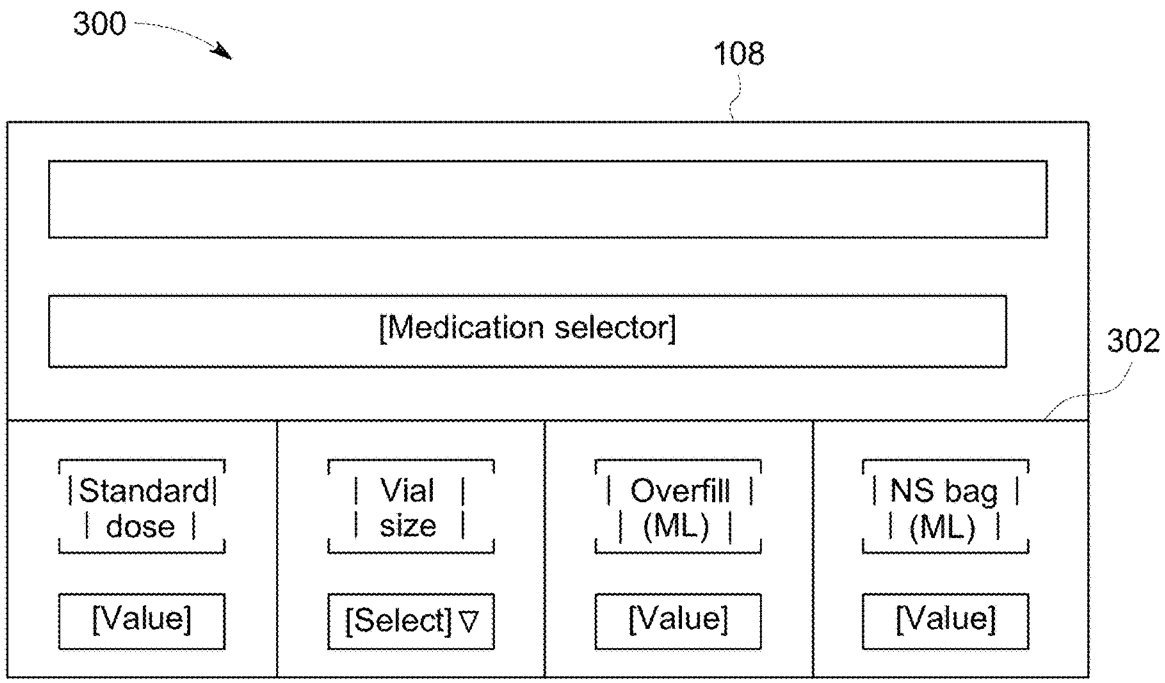
FIG. 3 illustrates a layout of a modular, bi-directional data architecture of medication setup interface, which is displayed on the user interface, in accordance with embodiments of the invention.

FIG. 3 refers to a layout 300 of a modular, bi-directional data architecture of medication setup interface which is displayed on the user interface 108. The medication setup interface. The medication setup interface provides a structured user interface for defining medication-specific preparation parameters used for automated infusion protocol generation. The medication setup interface is configured to present system identification and workflow stage information, a medication selection panel enabling selection of a pharmaceutical compound from a medication database, and a parameter input grid 302 comprising multiple configuration modules required for infusion preparation. The parameter input grid 302 includes a standard dose module, a vial configuration module, an overfill/residual volume module, and a diluent/infusion bag volume module. Each module includes a corresponding user input or display element facilitating data entry, calculated output display, or dropdown selection.

The medication setup interface enables automated infusion protocol computation, validation, calibration, and documentation. The database 124 supplies the medication setup interface 300, the dose evaluation module 110, and the vial optimization module 118 with drug-specific reference data. The dose evaluation module 110 processes user-defined and database-sourced parameters to compute infusion quantities and transmits the results to the multi-step protocol generation module, which constructs stepwise infusion sequences. The validation module 116 evaluates computed parameters against pre-configured therapeutic limits and provides real-time feedback through the user interface 108.

The calibration module 114 interfaces with the protocol generation module 112 to enable post-computation recalibration of infusion rate or total infusion time while maintaining dose and volume consistency. The document generation module 120 aggregates all user inputs, system evaluations, calibration outputs, and safety validation results to generate standardized, traceable pump programming documents for clinical use, optionally containing embedded machine-readable data for direct system programming.

Figure 4:
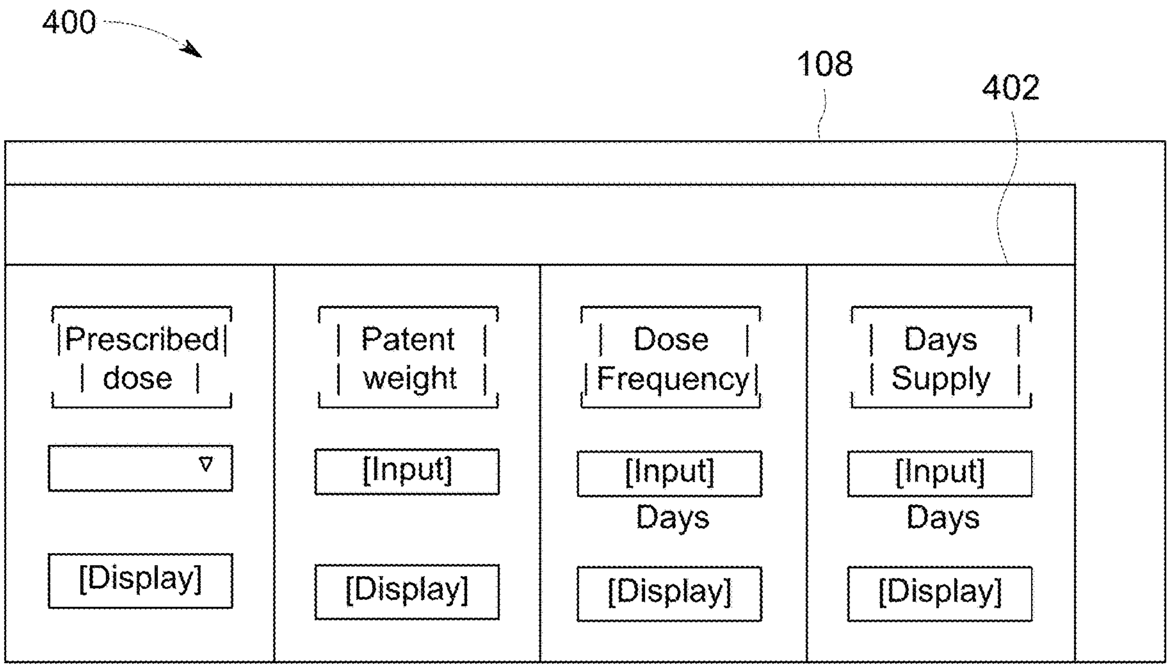
FIG. 4 illustrates a layout of the dose evaluation module, which is displayed on the user interface, in accordance with embodiments of the invention.

FIG. 4 refers to a layout 400 of the dose evaluation module 110 which is displayed on the user interface 108. The layout 400 includes a plurality of parameter input modules 402. A prescribed dose input module comprises an input field for receiving a dose value, a unit selection element for specifying a dosing unit, and an output display region for presenting a computed dose result. A patient weight module includes a weight input field and a corresponding formatted output display, and is configured to automatically convert between measurement units. A dose frequency module includes a frequency input field with an associated temporal unit indicator and an output display region for presenting a calculated dosing interval. A days-of-supply module includes an input field for defining a therapy supply duration and an output display for presenting a formatted summary of the supply period. Each module is configured to receive user input and generate a corresponding processed or calculated output, thereby providing a dual-layer input and display functionality.

In one embodiment, a dose evaluation process in which patient-specific parameters and medication information are processed to produce drug quantity and concentration values. User-provided inputs, including patient weight, prescribed dose amount, and dosing units, are received and evaluated via a decision logic to determine whether a weight-based dosing mode or a fixed-dose mode applies. In the weight-based mode, the prescribed dose value is multiplied by the patient's weight to determine the required drug quantity, whereas in the fixed-dose mode, the absolute dose value is utilized directly. The resulting calculated dose value is then provided to a concentration determination stage, in which infusion volume parameters are incorporated to compute final concentration and infusion rate values.

Figure 5:
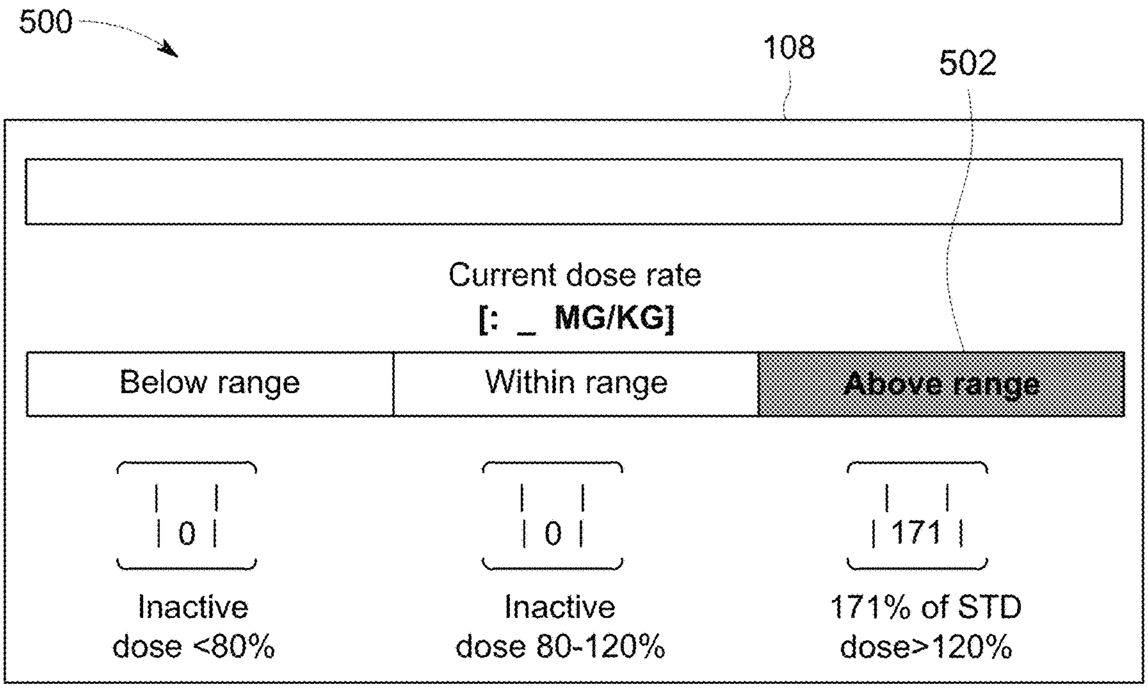
FIG. 5 illustrates a layout depicting the dose safety validation module, which is displayed on the user interface, in accordance with embodiments of the invention.

FIG. 5 refers to a layout 500 depicting the dose safety validation module 128 which is displayed on the user interface 108. The dose safety validation module 128 configured to provide dynamic, real-time visual feedback regarding dosing safety relative to a reference therapeutic range. The dose safety validation module 128 includes the semi-circular gauge display having a color-graduated region extending across approximately 180 degrees, transitioning from a first color indicative of an under-dosed state, through a second color indicative of a therapeutic state, to a third color indicative of an over-dosed state. A movable indicator or pointer is rendered over the gauge to denote the current dose position, and a numerical percentage value is displayed to reflect the calculated dose relative to a standard reference. A corresponding classification label is generated to describe the safety status. The gauge is dynamically updated as input parameters change to reflect the most recent dose evaluation.

The dose safety validation module 128 provides three operational states. Each state including a dose rate display module, a plurality of range indicator modules, and a gauge visualization module 502. Although structurally similar, each state presents different visual outputs corresponding to the calculated safety condition. In the above-range state, the calculated dose value exceeds an upper safety threshold (e.g., above 120% of a reference standard), causing activation of an above-range indicator and a corresponding gauge reading reflecting a value of 171%. In the within-range state, the calculated dose value lies within an acceptable therapeutic range (e.g., 80-120% of the standard), activating the within-range indicator and displaying a gauge reading of 109%. In the below-range state, the calculated dose value is lower than the therapeutic threshold (e.g., below 80% of the standard), activating the below-range indicator and displaying a gauge reading of 5%.

Across all states, the gauge visualization modules provide a semi-circular scale with a fill or shading representation corresponding to the percentage value relative to the standard reference. Inactive indicators in any given state are visually de-emphasized, while the active indicator is visually accentuated. The infusion pump programming system 100 thereby provides continuous, real-time dose safety validation and classification across multiple operational thresholds.

Figure 6:
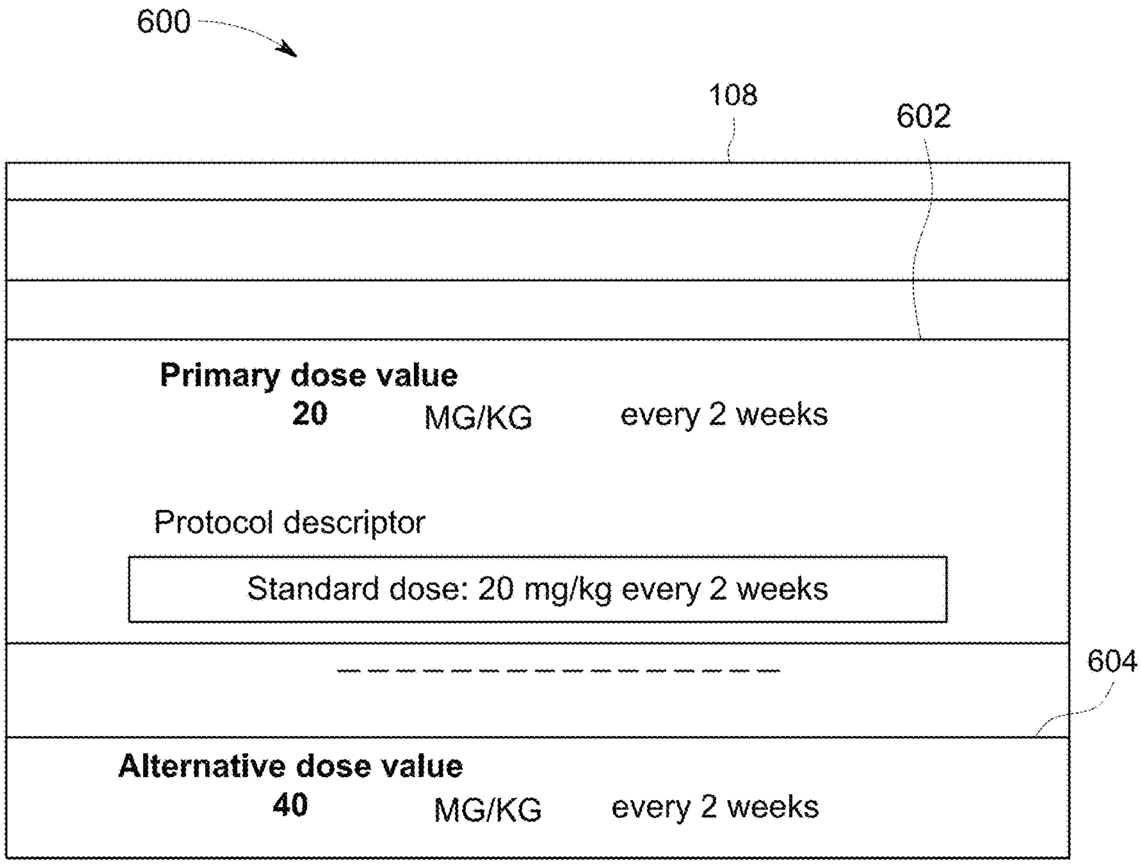
FIG. 6 illustrates a layout depicting special dosing options system, which is displayed on the user interface, in accordance with embodiments of the invention.

FIG. 6 refers to a layout 600 depicting special dosing options system which is displayed on the user interface 108. The special dosing options system comprises a plurality of dosing option modules (602, 604). Each dosing option module comprises a dose value assembly including a numeric dose value element, a dose unit indicator, and a temporal frequency indicator for defining the dosing schedule. The dose value elements are presented in a format that facilitates rapid visual recognition and minimizes the likelihood of transcription or selection errors. A protocol descriptor field is associated with the primary dosing option module 602 and provides a textual specification of the standard dosing regimen, while an alternative dosing option module 604 includes a condition identifier field for specifying a clinical condition and its corresponding dosing parameters. The structural configuration of the modules is arranged to enable clear differentiation between standard and special-condition dosing selections, thereby supporting correct protocol identification in clinical use environments. The modular architecture further permits additional dosing options to be incorporated by replicating the module structure with corresponding identifiers.

FIG. 6 illustrates a form-based data structure representing a medication database schema. The schema includes fields for storing medication identification information, an array of vial size configurations, reconstitution and dilution parameters, concentration limits, and one or more special dosing protocol definitions. The data structure is configured to support retrieval and application of both standard and condition-specific dosing instructions within the infusion pump programming system 100.

Figure 7:
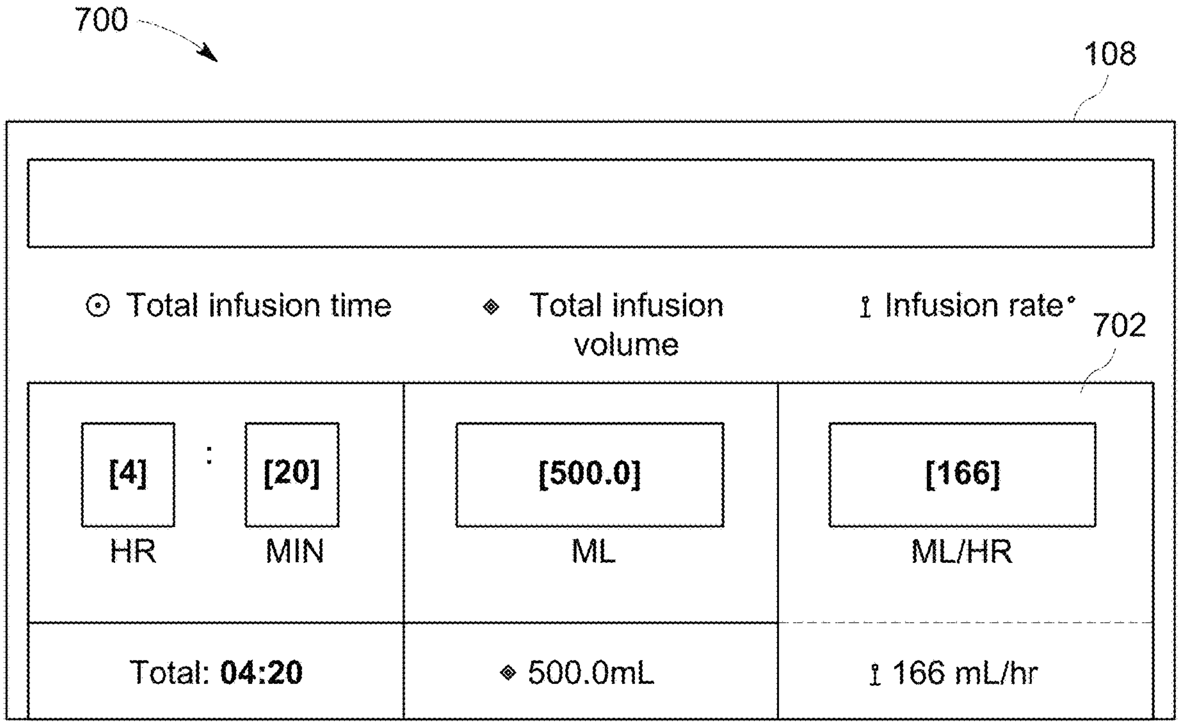
FIG. 7 illustrates a layout depicting the protocol generation module, which is displayed on the user interface, in accordance with embodiments of the invention.

FIG. 7 refers to a layout 700 depicting the protocol generation module 112 which is displayed on the user interface 108. The protocol generation module 112 includes a plurality of parameter entry modules 702 configured to receive and process infusion-related inputs. The infusion pump programming system 100 comprises a time input module having an hour input field and a minute input field for defining a target infusion duration, a volume input module including a volume input field for specifying an infusion volume, and a rate module including a rate field for defining or adjusting an infusion rate. Each module includes associated unit identifiers to ensure clear parameter interpretation. The infusion pump programming system 100 is configured such that the infusion rate field may operate in a calculated mode or in a user-adjustable mode, allowing the infusion rate to be automatically determined based on the time and volume inputs or manually modified to support specific clinical protocols.

The protocol generation module 112 further includes output display regions configured to present processed or calculated values based on the parameters received. The time display generates a standardized representation of the infusion duration. The volume and rate displays provide updated values corresponding to the applied infusion configuration, enabling real-time feedback as input parameters change. The infusion pump programming system 100 thereby supports interdependent parameter management wherein modification of any one of the time, volume, or rate parameters results in automatic reevaluation of at least one of the remaining parameters, facilitating accurate and safe infusion planning.

FIG. 7 illustrates a dose evaluation process in which patient-specific data and medication information are processed to determine required drug quantities and concentration values. User inputs such as patient weight, prescribed dose amount, and dose units are received and processed through a decision stage that determines whether a weight-based or fixed-dose evaluation pathway applies. In the weight-based pathway, the prescribed dose value is multiplied by the patient's weight to generate the required drug quantity, whereas the fixed-dose pathway applies the specified dose directly. Both pathways converge at a concentration determination stage in which infusion volume parameters are incorporated to compute a resulting concentration and infusion rate.

Figure 8:
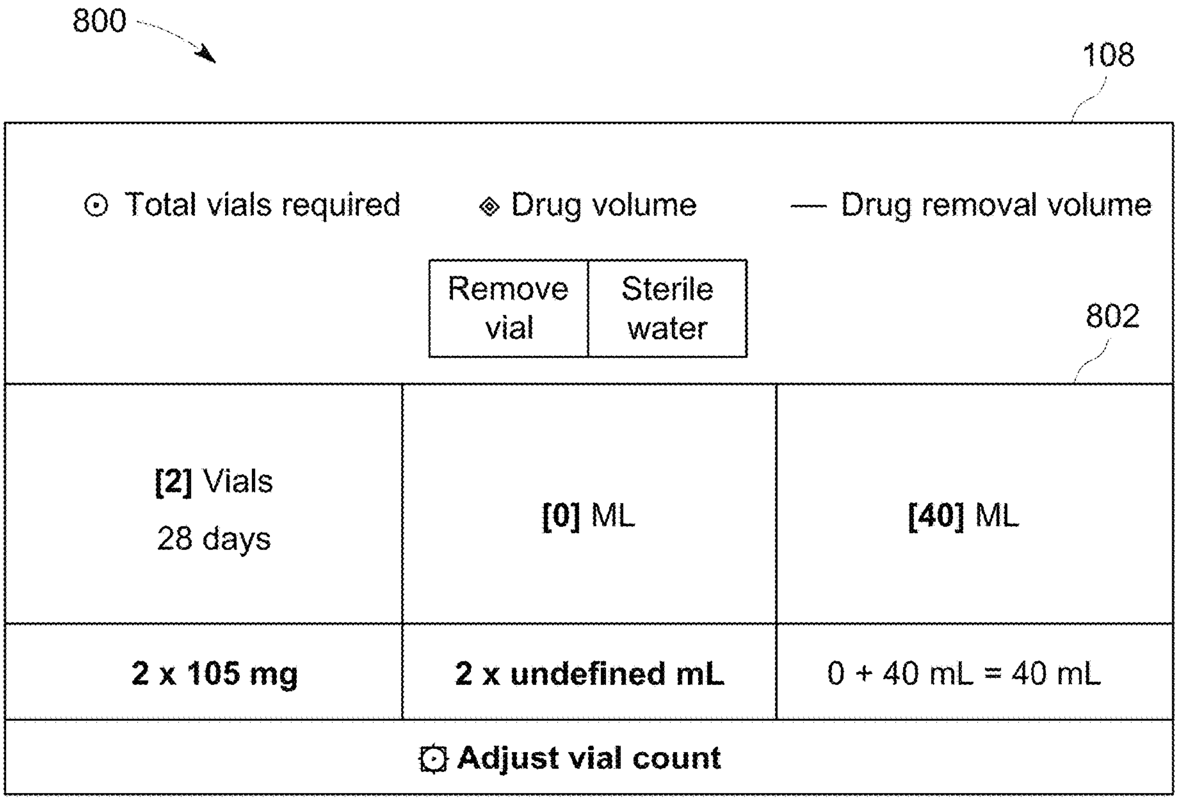
FIG. 8 illustrates a layout depicting the vial optimization module, which is displayed on the user interface, in accordance with embodiments of the invention.

FIG. 8 refers to a layout 800 depicting the vial optimization module 118 which is displayed on the user interface 108. The vial evaluation and adjustment system includes two operational states. A first state 802 provides a primary vial evaluation interface comprising a vial requirement module, a drug volume module, and a removal volume module. Each module includes one or more input and output fields configured to receive vial-related parameters and present corresponding calculated values. The infusion pump programming system 100 further includes an adjustment initiation control that, when activated, transitions the interface to an adjustment state for vial configuration modification.

A second state (not shown) provides a vial count adjustment interface that includes a drug identification field, and a required dose display. A current combination display presents the active vial configuration. An adjustment control module includes decrement and increment controls and a numeric display for modifying the vial count. A plurality of action controls is provided, including a rounding-up control, a rounding-down control, an open-vial volume control, a reset control, and an apply control. The adjustment interface is configured to enable focused modification of vial quantities while maintaining contextual awareness of the current evaluation state.

In one embodiment, the infusion pump programming system 100 includes a plurality of parameter modules configured to receive or display infusion-related values. The parameter modules include a prime volume module having an input field for specifying a priming volume, a flush volume module having an input field for specifying a post-infusion flush volume, an infusion mode module including a toggle control assembly for selecting an infusion mode, an overfill value module including an input field for entering an overfill value, a drug volume module including a display field for presenting a calculated drug volume, and a volume-to-remove module including a display field for presenting a calculated removal volume. The infusion mode toggle assembly includes a descriptive text element and a binary selection control configured to enable a user to select between infusion preparation modes associated with overfill management.

In some embodiments, the infusion pump programming system 100 includes a dead-space compensation algorithm that adjusts the post-infusion flush volume to account for residual fluid remaining in pump tubing and connectors. The database 124 stores device-specific dead-space volumes, which typically range from 0.2 to 1.5 mL depending on pump model and tubing length. During protocol finalization, the infusion pump programming system 100 automatically increases the flush step volume by the dead-space amount to ensure complete medication delivery.

The infusion pump programming system 100 is configured such that the input fields receive user-specified parameters, while the display fields present calculated values that are automatically updated based on the input parameters and the selected infusion mode. The arrangement of the modules enables sequential review and verification of infusion preparation parameters, thereby reducing the likelihood of input or transcription errors during clinical use. The architecture further supports expansion to incorporate additional infusion preparation parameters without altering the operational framework of the infusion pump programming system 100.

In one embodiment, the vial optimization module 118 incorporates a multi-strategy dynamic optimization engine configured to compute optimal vial combinations for a prescribed drug dose. The multi-strategy dynamic optimization engine does not rely on traditional single-path optimization methods such as greedy algorithms or dynamic programming.

Instead, the vial optimization module 118 simultaneously generates and evaluates four distinct optimization strategies, each producing a complete vial-combination solution. The optimization strategies comprise a vial-count minimization strategy, a waste minimization strategy, a balanced mixed strategy, and an exhaustive combination search strategy. These candidate solutions are then ranked using a multi-criteria decision analysis (MCDA) framework incorporating weighted factors such as vial count, drug waste, cost, and preparation efficiency. The MCDA module is configured to rank the candidate solutions based on a plurality of weighted factors including vial count, waste volume, drug cost, preparation complexity, and institutional preference profiles. The MCDA module selects as a final recommendation the candidate solution having the highest aggregate weighted score.

This architecture allows the vial optimization module 118 to produce a globally optimal recommendation across the entire solution space, rather than converging on a locally optimal or subproblem-derived solution typical of greedy or dynamic programming approaches. The multi-strategy dynamic optimization engine ensures robustness, consistency across dose ranges, and adaptability for drugs supplied in multiple vial strengths.

In one embodiment, the vial-count minimization strategy computes a vial selection that minimizes the total number of vials required for the prescribed dose. This reduces handling effort, preparation burden, and overall compounding complexity. The vial optimization module 118 applies a 0.01 mL rounding-up threshold, ensuring that any clinically relevant remainder results in the addition of one full vial to prevent underdosing.

In one embodiment, the waste minimization strategy prioritizes minimization of drug wastage by selecting a vial combination whose cumulative volume exceeds the prescribed dose by the smallest possible amount. This strategy is particularly suited for costly biologics and specialty medications where waste reduction directly impacts economic efficiency.

In one embodiment, the balanced mixed strategy generates a balanced trade-off between vial count and waste volume. The multi-strategy dynamic optimization engine computes combinations by simultaneously applying constraints related to minimizing excess volume while avoiding excessive vial counts. This produces a clinically practical middle ground when neither extreme minimal waste nor minimal count is ideal.

This approach evaluates both vial count and waste volume simultaneously using weighted scoring:

$$\text{Score} = \alpha(vialCount) + \beta(wasteVolume)$$

In one embodiment, the exhaustive combination search strategy performs an exhaustive search across all mathematically valid vial combinations. The vial optimization module 118 evaluates every feasible combination to identify either an exact match to the prescribed dose, or a combination producing the lowest possible non-zero waste within allowable tolerances. This comprehensive evaluation ensures the multi-strategy dynamic optimization engine does not miss combinations that single-path optimizers or heuristic methods would fail to identify.

After the four strategies generate their respective solutions, the vial optimization module 118 executes a parallel evaluation and scoring process using weighted decision factors. In one embodiment, the evaluated using a dual-criteria ranking algorithm prioritizing waste minimization followed by vial-count minimization. These may include total vial count, total waste volume, preparation time, drug cost, and institutional preference profiles. The strategy with the highest weighted score is selected as the final optimized recommendation. The vial optimization module 118 may also display secondary options to give clinicians visibility into alternative vial usage patterns.

In one embodiment, the vial optimization module 118 performs supply-period integration, computing total drug requirements over a full treatment duration using:

$$\text{total Drug Needed} = \text{single Dose} \times \text{ceil}\left(\frac{\text{days Supply}}{doseFrequency}\right)$$

where single Dose represents the prescribed dose per administration, days Supply represents the total treatment period, and dose Frequency represents the interval in days between doses. The ceiling function ensures sufficient medication for all scheduled administrations.

The vial optimization module 118 computes the number of days covered by available vials:

$$\text{days Covered} = \text{floor}\left(\frac{\text{total Drug Available}}{\text{daily dose}}\right)$$

where total Drug Available represents the sum of medication quantities from selected vials, and daily Dose represents the daily medication requirement. The floor function conservatively estimates coverage duration to prevent inadequate supply.

The multi-strategy dynamic optimization engine performs precise remainder analysis for vial allocation using a 0.01 mL clinical threshold. If remainder $>0.01 \rightarrow$ round up (add vial). If remainder $\leq 0.01 \rightarrow$ round down (no vial added).

In one embodiment, the multi-strategy dynamic optimization engine computes the remainder volume after allocating the maximum integer number of vials for a given dose. When the computed remainder exceeds 0.01 mL, the vial optimization module 118 automatically triggers an additional vial allocation to ensure adequate therapeutic supply; conversely, when the remainder is 0.01 mL or less, the vial optimization module 118 classifies the remainder as clinically negligible and suppresses any additional vial addition.

The vial optimization module 118 further incorporates an intelligent alternative-generation mechanism that activates whenever predefined clinical or operational thresholds are exceeded. When the calculated waste percentage surpasses 20%, or when the computed days of coverage fall below the required treatment period, the vial optimization module 118 automatically retrieves the previously ranked set of vial-combination solutions and generates a curated list of top-ranked alternatives. These alternatives are displayed with corresponding waste metrics, coverage projections, and accuracy indicators to support clinician decision-making.

In a preferred embodiment, the vial optimization module 118 evaluates the complete solution space generated by all parallel optimization strategies rather than relying on sequential or locally optimal decision paths.

In one embodiment, the vial optimization module 118 ranks all candidate vial-combination solutions generated by the four optimization strategies using a two-level evaluation framework. At the first level, the vial optimization module 118 applies a primary criterion of waste minimization, sorting candidate solutions in ascending order of excess volume. A secondary criterion of vial-count minimization is then applied as a tiebreaker to discriminate between solutions with equivalent waste values. Each strategy-minimize-vial-count, minimize-waste, balanced-mix, and exhaustive-combination-search-independently generates a complete and viable candidate solution. The vial optimization module 118 aggregates the candidate outputs from all strategies and performs a global evaluation using multi-criteria ranking logic, selecting the combination that provides the highest clinical and operational utility. This global-optimization methodology yields superior results relative to traditional greedy or sequential decision processes, which evaluate choices incrementally and fail to account for the full solution space of feasible dose-matching combinations.

The vial optimization module 118 continuously monitors waste percentage, dose accuracy percentage, and coverage percentage. Trigger conditions waste percentage >20%, accuracy ratio <95% or >105%, and days covered <days supply. Upon detection, the vial optimization module 118 automatically generates top 3 alternative vial combinations.

The vial optimization module 118 provides a real-time interactive dashboard displaying Dose Accuracy Gauge, Waste Volume Indicator, and Coverage Progress Bar. Each uses independent color-coding green (optimal), yellow (warning), and red (alert). The dashboard updates instantly when any parameter changes.

In one embodiment, table 4 depicts intelligent thresholds for adaptive multi-metric decision monitoring.

TABLE 4

| Metric | Threshold | System Action |
|---|---|---|
| Waste Percentage | >20% | Display warning: "Consider different vial combination." |
| Dose Accuracy | 95-105% | Optimal range (green status). |
| Dose Accuracy | <95% | Attention required (yellow) - underdosing. |
| Dose Accuracy | >105% | Review required (red) - overdosing. |
| Days Coverage | <required supply | Display: "Need X more days of coverage." |
| Round-up Threshold | >0.01 | Any remainder >0.01 triggers additional vial. |

Figure 9:
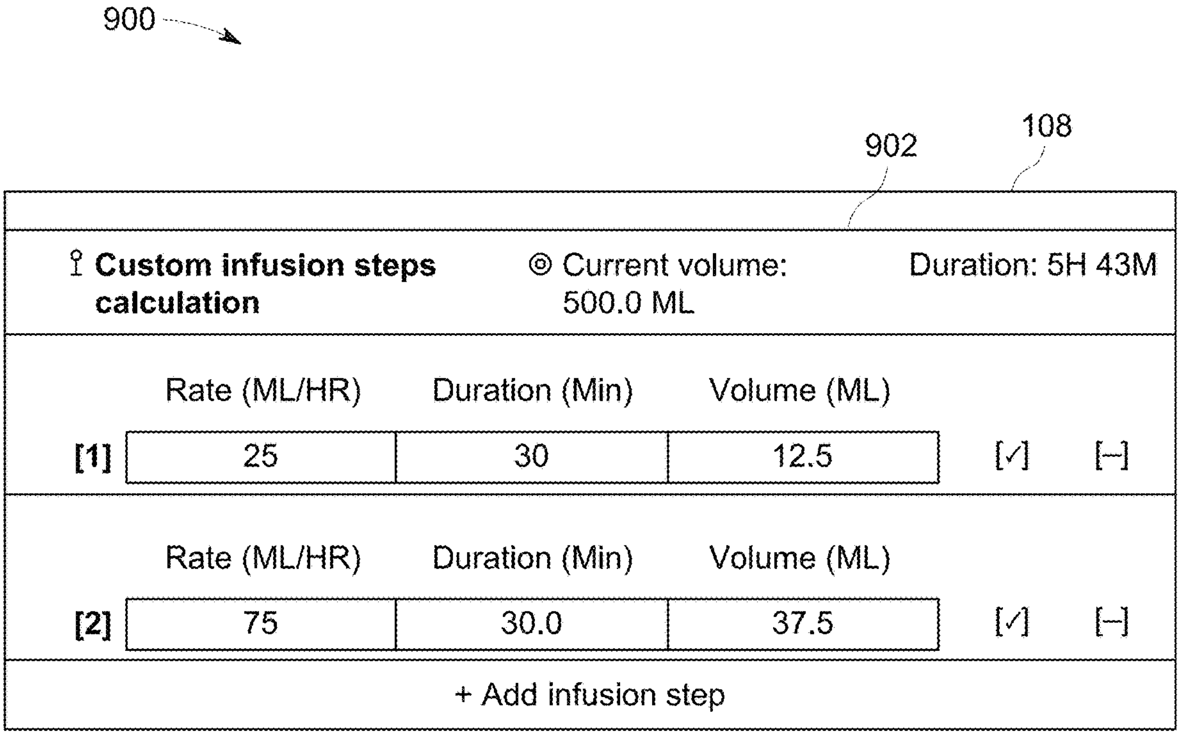
FIG. 9 illustrates a layout depicting custom infusion steps, which is displayed on the user interface, in accordance with embodiments of the invention.

FIG. 9 refers to a layout 900 depicting custom infusion steps which is displayed on the user interface 108. The custom infusion steps, including sequential phases of infusion such as an initial flush phase, a ramp-up phase, a main infusion phase, a ramp-down phase, and a terminal flush phase. Each phase is defined by a corresponding step including a rate value, a duration value, and a resulting volume contribution. The infusion pump programming system 100 performs automatic validation of each step's parameters, including ensuring that step-specific rate and duration values produce a calculated volume consistent with the overall infusion plan and that the aggregated values across all steps match the total infusion volume and total infusion time specified for the protocol.

The layout 900 includes a volume display, a rate display, and a duration display. The infusion pump programming system 100 further comprises a plurality of infusion step modules 902, each corresponding to a sequential infusion step within a multi-step protocol. Each infusion step module includes a step identifier, a rate input field, a duration input field, a volume display field, and one or more control for modifying or managing the step. One or more of the later steps, such as steps 4 and 5, may include information indicators to denote parameters that are system-generated or derived based on preceding step inputs and total infusion constraints.

The infusion pump programming system 100 is configured to automatically compute the infusion volume for each step based on the entered rate and duration values and to update cumulative infusion time and volume across all steps. The architecture allows dynamic modification of step parameters, and a step-addition control enables expansion of the sequence to include additional infusion steps beyond the initial configuration. The infusion pump programming system 100 may also validate step parameters to ensure internal consistency, including compliance with total infusion volume, total infusion time, and rate-transition logic, and may generate alerts or prevent progression when inconsistencies are detected.

The validation status display represents a confirmation state generated upon successful validation of a custom multi-step infusion configuration, such as that shown in FIG. 9. A plurality of validation confirmation modules is provided to display detailed verification results relating to distinct aspects of the infusion protocol. Each validation confirmation module includes an indicator element and an associated descriptive field that identifies the specific validation performed. A first validation confirmation module verifies that each infusion step satisfies system rules and constraints. A second validation confirmation module verifies that the total calculated infusion volume matches the intended target volume. A third validation confirmation module verifies that the calculated total infusion duration is consistent across multiple time formats or representations and falls within an acceptable tolerance threshold. The validation state is displayed as a distinct interface layer relative to the primary configuration interface to indicate completion of the validation cycle prior to clinical use.

This validation mechanism confirms the internal consistency of all infusion parameters, including per-step and cumulative values, and ensures compliance with system-defined safety constraints. By providing confirmation of evaluation accuracy and configuration integrity, the infusion pump programming system 100 reduces the likelihood of infusion programming errors and enhances patient safety.

In one embodiment, a fixed infusion evaluation functionality of the infusion pump programming system 100 is configured to receive user-provided inputs relating to medication dosing, patient parameters, and infusion requirements, and to automatically generate a fixed-rate infusion protocol suitable for pump programming. Upon initiation, the infusion pump programming system 100 validates the input parameters, including patient weight, prescribed dose (expressed as either an absolute value or a weight-based value in mg/kg), and the total infusion volume. Based on the validated dose requirement, the infusion pump programming system 100 employs a dynamic programming-based vial selection process to determine an optimal vial combination that minimizes medication waste. The infusion pump programming system 100 subsequently calculates the drug volume required using the medication concentration and determines whether the infusion will be prepared by adding the drug to an empty infusion container or by removing a portion of diluent from a pre-filled infusion container.

For a remove-overfill mode, the infusion pump programming system 100 calculates the volume of diluent that must be withdrawn from the pre-filled container to maintain the target total infusion volume following drug addition. For an add-to-empty mode, the infusion pump programming system 100 determines the volume of diluent required to dilute the drug to the target concentration for administration. The infusion rate is computed by dividing the total infusion volume, excluding the prime volume, by the target infusion duration to produce a fixed-rate protocol in which the medication is infused at a constant programmed rate followed by a flush step.

The infusion pump programming system 100 further performs safety and compliance checks, including dose-range verification, compatibility of the calculated rate with infusion pump specifications, and confirmation that the prepared volume and concentration align with safety thresholds. Following validation, the infusion pump programming system 100 generates step-wise pump programming instructions that include priming volume administration, the main infusion at the calculated fixed rate, and delivery of the flush volume. Throughout the process, the infusion pump programming system 100 records and verifies the administered dose relative to the prescribed dose for traceability and clinical safety assurance.

FIG. 10 a layout 1000 depicting a document generation process, which is displayed on the user interface 108. The document generation process in which a pump programming record is created, encoded, and delivered. The process is initiated upon activation of a document-generation command. In response, the infusion pump programming system 100 aggregates all required parameters, including user-entered data and automatically validated infusion evaluation results obtained from associated modules. A machine-readable data object is then generated and encoded, for example as a QR code, containing structured infusion parameters in a JSON format.

Following data acquisition, the infusion pump programming system 100 generates a document object using the document generation module 120, such as a DOCX generation library, and constructs one or more tables populated with the collected parameters and formatted according to predefined document templates. The QR code image is embedded within the document as a verification and rapid-import mechanism. A file name is then generated using one or more identifiers, which may include patient information, medication name, protocol version, or timestamp, to ensure unique file creation and traceability. Upon completion of the document assembly, the infusion pump programming system 100 triggers a delivery action that may include initiating a browser-based file download, transmitting the document via email, or exporting the pump programming sheet to external systems for clinical use.

In one embodiment, a mathematical relationship system is configured to maintain the triangular computational relationship between infusion rate, infusion volume, and infusion time, wherein entry of any two parameters enables automatic evaluation of the third. The infusion pump programming system 100 performs continuous validation of the interdependent parameters and provides real-time feedback indicating whether the entered values satisfy defined constraints and clinical safety requirements.

In one embodiment, a validation state flow operates as follows. An initial state awaits user input. Upon entry or modification of one or more parameters, an input-trigger state initiates the validation process. A validation logic stage evaluates the parameter values to confirm that they fall within permitted ranges and comply with the mathematical relationships between rate, volume, and time. When all validation checks are satisfied, the infusion pump programming system 100 transitions to a valid state, enabling automatic evaluation of the remaining parameter. If a validation failure is detected, the infusion pump programming system 100 transitions to an error state in which a descriptive message identifies the validation failure. An error-resolution state enables correction of the input and returns the infusion pump programming system 100 to the valid state once the issue is resolved. The validation cycle repeats upon each subsequent parameter modification.

Figure 11:
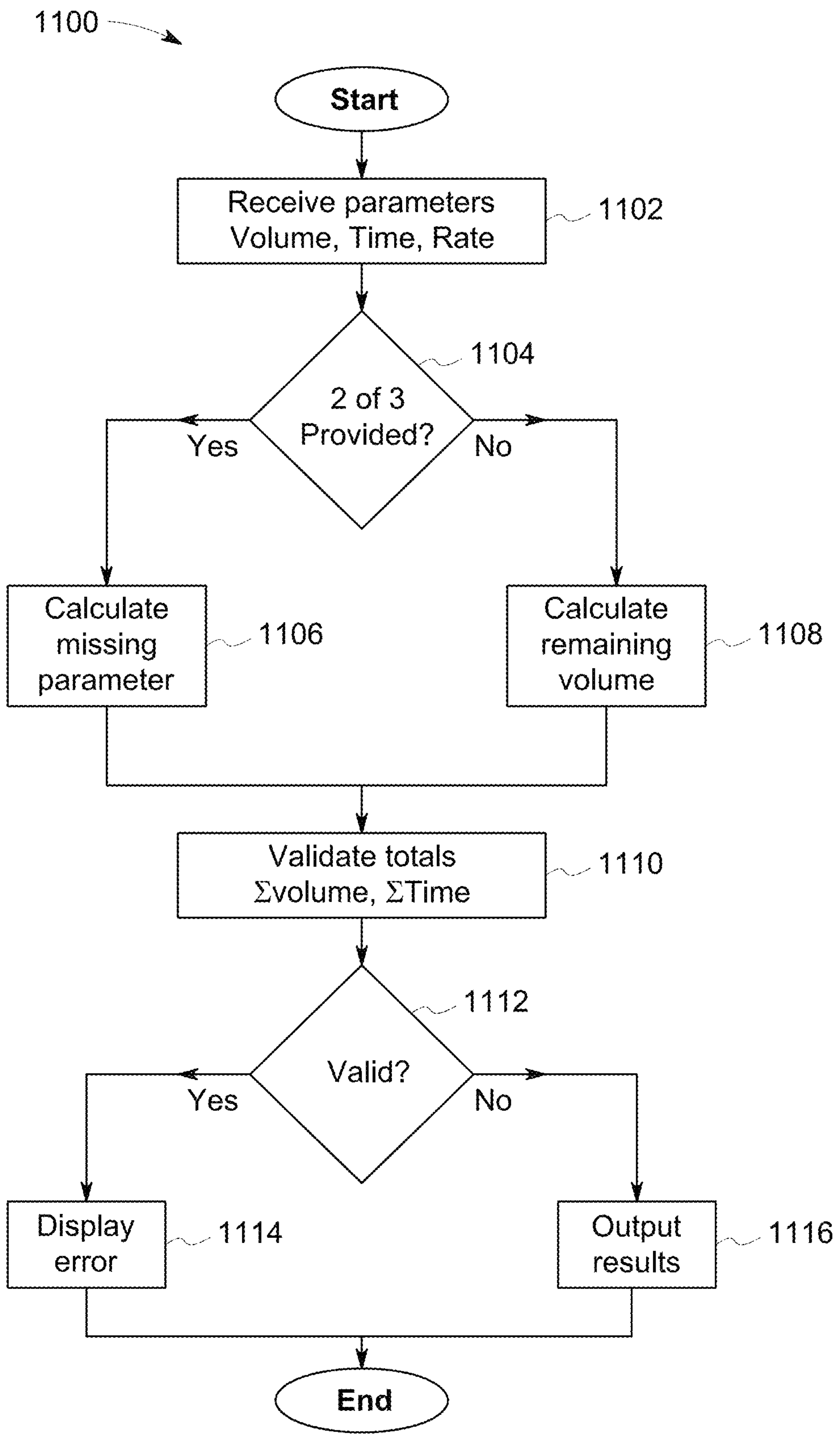
FIG. 11 illustrates a flowchart for an infusion parameter determination process, in accordance with embodiments of the invention.

FIG. 11 refers to a flowchart 1100 for an infusion parameter determination process configured to compute an infusion parameter based on the triangular computational relationship between infusion volume, infusion time, and infusion rate. The process begins at step 1102, in which the infusion pump programming system 100 receives one or more infusion parameters, including infusion volume, infusion time, and infusion rate. At decision step 1104, the infusion pump programming system 100 determines whether at least two of the three parameters have been provided.

If at least two parameters are available, the process proceeds to step 1106. The infusion pump programming system 100 calculates the missing parameter using mathematical relationships between volume, time, and rate. If fewer than two parameters are provided, the process proceeds to step 1108. The infusion pump programming system 100 calculates a remaining value based on predefined system rules or default infusion conditions.

Following parameter computation, the process advances to step 1110, where the infusion pump programming system 100 validates the calculated totals, including total infusion volume and total infusion time, to ensure consistency with system rules and clinical safety constraints. At decision step 1112, the infusion pump programming system 100 determines whether the parameters satisfy validation criteria. If validation fails, the process transitions to step 1114, where an error condition is generated and a corresponding error notification is provided through the user interface 108. If validation is successful, the process proceeds to step 1116, where the infusion pump programming system 100 outputs the validated results for use in infusion programming or further processing. The process then terminates.

In one embodiment, an infusion parameter configuration process in which total infusion time, total infusion volume, and infusion rate values are received and processed. The process begins with user inputs including total infusion time and total infusion volume, and optionally an infusion rate value for fixed-rate infusions. The infusion pump programming system 100 calculates any dependent parameter as required, such that modification of one parameter results in automatic adjustment of at least one of the remaining parameters to maintain internal consistency of infusion configuration.

In one embodiment, a vial combination optimization process utilizing a dynamic programming approach in which possible vial size combinations are generated, evaluated, and ranked to identify an optimal configuration. Based on a required dose input, the infusion pump programming system 100 accesses available vial size data and generates combinations up to a defined maximum vial count. For each combination, a waste value is computed based on unused medication volume. A ranking module sorts combination according to waste percentage or other prioritization criteria, enabling presentation of one or more preferred options. The infusion pump programming system 100 supports automatic selection of a minimally wasteful vial configuration as well as user-directed override functions, including rounding to the nearest vial size or applying alternative vial counts, in order to accommodate clinical preferences or specific medication handling requirements. The optimization logic further accounts for drug withdrawal volume, infusion preparation protocols, and whether the drug is drawn directly from vials or prepared through dilution with sterile fluid.

In one embodiment, the infusion pump programming system 100 is industrially applicable to the preparation and programming of infusion therapies in clinical, pharmaceutical, and veterinary settings. It may be manufactured and utilized in hospitals, outpatient centers, pharmacies, home healthcare services, and training institutions for generating accurate infusion protocols and pump programming documentation. The infusion pump programming system 100 is capable of being implemented in existing infusion workflows and provides reliable technical effects related to dosing accuracy, documentation, and patient safety.

In one embodiment, the infusion pump programming system 100 has wide commercial applicability across hospitals, outpatient centers, pharmacies, and home-care infusion services. The infusion pump programming system 100 substantially reduces staff time spent on manual infusion evaluations and documentation, resulting in measurable labor cost savings and increased operational throughput. By optimizing vial selection, infusion parameter evaluations, and protocol preparation, the infusion pump programming system 100 minimizes drug wastage and consumable use, thereby reducing direct medication preparation costs. The infusion pump programming system 100 further enhances revenue opportunities for infusion providers by shortening preparation time, enabling higher patient turnover, and supporting multi-patient batch processing without compromising accuracy or safety. Institutions benefit from improved documentation quality, reduced training time for new staff, and standardized workflows that decrease dependency on highly skilled clinical pharmacists for routine evaluations.

In one embodiment, the infusion pump programming system 100 that provides an integrated, processor-implemented platform for automating infusion therapy preparation and pump programming. The infusion pump programming system 100 includes the database 124 configured to store medication records, vial configurations, dosing parameters, and protocol constraints, and the dose evaluation module 110 configured to compute weight-based, fixed-dose, and multi-step infusion protocols including priming, ramp-up, main infusion, ramp-down, and flushing steps. The vial optimization module 118 implements a dynamic programming-based algorithm to determine vial combinations that minimize medication waste. The dose safety validation module 128 is configured to provide real-time therapeutic range assessment via the user interface 108 employing color-coded indicators to reflect dose safety status. The infusion pump programming system 100 automatically calculates infusion rates, delivered volumes, step durations, drug removal or overfill adjustments, and priming volume requirements based on selected dosing parameters.

In one embodiment, the user interface 108 is configured to display a validation passed message upon successful verification of the infusion protocol. The message comprises confirmation that all infusion steps are valid, a total volume evaluation showing equivalence between a sum of step volumes and target infusion volume, and a total duration evaluation showing equivalence between a sum of step durations and expected total infusion time.

In one embodiment, the infusion pump programming system 100 further includes the calibration module 114 configured to adjust calculated infusion parameters post-computation in response to user-initiated rate or time recalibration, and the document generation module 120 configured to produce pump-programming records encoded with machine-readable data for clinical verification and use. The infusion pump programming system 100 supports the entry, versioning, and persistent storage of custom medication profiles and special-use infusion protocols to accommodate non-standard or institution-specific requirements. By automating dosing evaluations, calibration operations, safety validation, and documentation workflows, the infusion pump programming system 100 reduces manual computation and transcription errors, standardizes infusion programming, and enhances clinical safety and efficiency in infusion therapy administration.

In one embodiment, the infusion pump programming system 100 automates the recalibration of multi-step infusion protocols whenever rate, volume, or total infusion time is modified, eliminating manual re-entry and reducing evaluation errors. The infusion pump programming system 100 preserves the clinical logic and sequencing of infusion steps such as ramp-up, main infusion, ramp-down, and flush phases ensuring that safety thresholds and dosing rules remain intact during reevaluation. By integrating dose evaluation, vial optimization, protocol generation, calibration, safety validation, and documentation into a single end-to-end workflow, the invention minimizes workflow fragmentation and prevents transcription errors. The vial optimization feature further reduces drug wastage, particularly for high-cost medications, by determining the most efficient vial combination. Real-time safety validation and infusion-rate checks provide immediate feedback to prevent unsafe dosing. In addition, machine-readable, standardized pump programming documents, including QR-encoded infusion data, enhance traceability and clinical documentation accuracy. The infusion pump programming system 100 supports both standard and custom infusion regimens, enabling flexibility while maintaining safety controls, and is applicable across diverse care settings including hospitals, outpatient infusion centers, home infusion services, clinical research, and veterinary medicine, thereby improving efficiency, accuracy, and safety in infusion therapy administration.

FIGS. 12A-12F refer to schematic layouts (1200, 1202, 1204, 1206, 1208, 1210) for an infusion parameter determination process layout enabling entry and customization of multi-step infusion parameters. In an exemplary embodiment, reference to FIG. 12A, an infusion is prepared for a patient having a body weight of 92.53 kg. A prescribed medication, Drug X, is to be administered intravenously at a dosage of 100 mg in 250 ml of normal saline on a bi-weekly schedule. In this embodiment, the infusion pump programming system 100 receives patient-specific information and infusion parameter inputs through the user interface 108. To compensate for the drug volume and saline bag overfill, 80 ml of normal saline is withdrawn from the 250 ml saline bag. Subsequently, 50 ml of the drug solution is introduced into the primary saline bag. A priming volume of 10 ml is prepared, resulting in a final total infusion volume of 250 ml. The infusion pump is pre-programmed with variable pump settings suitable for the prescribed infusion protocol.

Figure 12A:
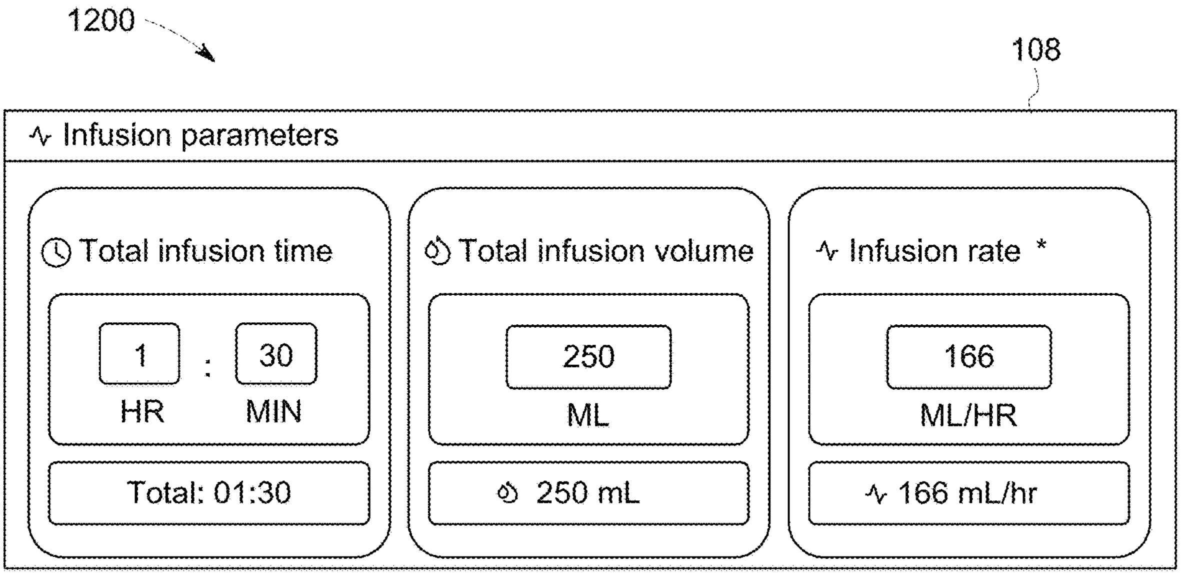
FIGS. 12A-12F refer to schematic layouts for an infusion parameter determination process layout enabling entry and customization of multi-step infusion parameters, in accordance with embodiments of the invention.
Figure 12B:
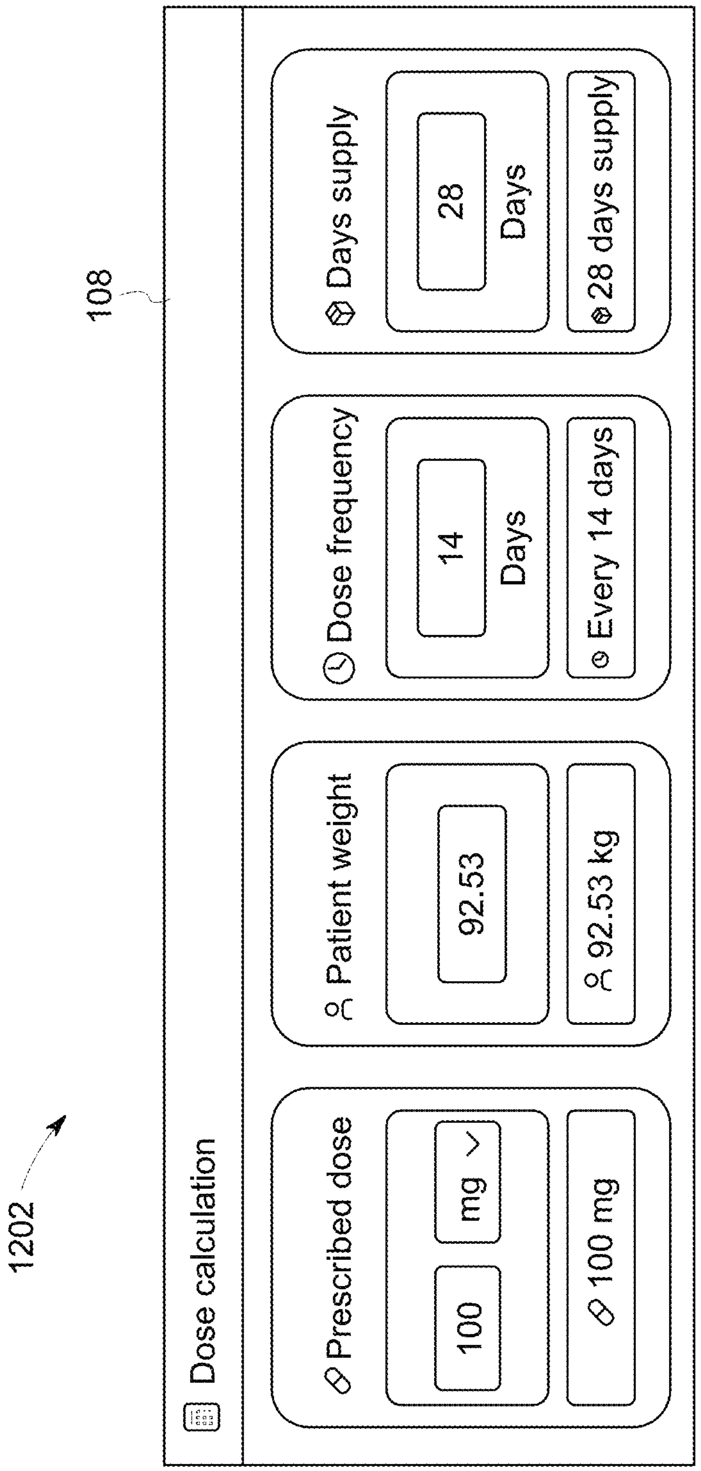

With reference to FIG. 12B, the dose evaluation module 110 is configured to calculate the required amount of the medication based on patient-specific inputs. The patient-specific inputs include, at minimum, the patient's body weight and the prescribed dosage.

To initiate the infusion, the infusion pump is powered on to allow a review of the programmed settings, and a warm-up cycle is completed. The user then confirms the prescription by pressing "Enter" and reconfirms by pressing "Enter" again to validate the programmed instructions. The infusion pump thereafter executes the programmed infusion sequence automatically. Once priming is completed and the IV line is connected, the "Run" command is selected to commence the infusion. The programmed sequence includes a first phase in which 240 ml of the solution is infused at a rate of 166 ml/hr, followed by a second phase in which a 10 ml flush is administered at the same rate. The flush is added through the additive port of the IV bag upon completion of the first phase. The total infusion duration is approximately 1 hour and 30 minutes.

Figure 12C:
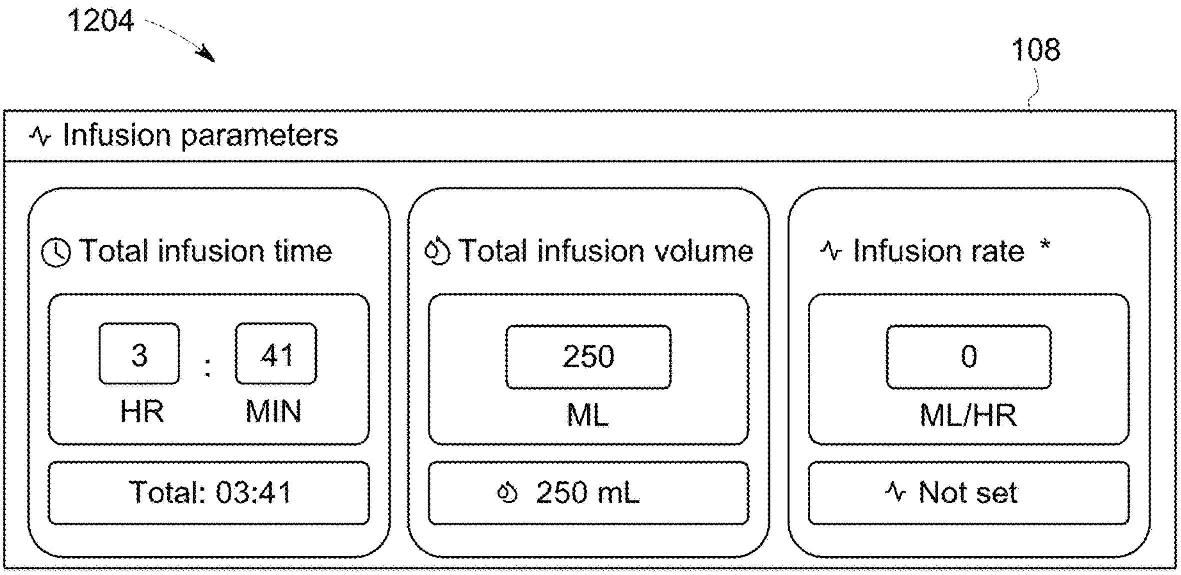

In another exemplary embodiment, reference to FIG. 12C, a patient weighing 43.09 kg is scheduled to receive a prescribed medication, Drug Y, infusion of 900 mg every two weeks. For preparation, 120 ml of diluent is removed from a 250 ml D5W IV bag to account for the drug and overfill volume. A total of 90 ml of the drug solution is then added to the primary D5W bag, wherein each vial of Drug Y is reconstituted with 10 ml of sterile water prior to mixing. A priming volume of 10 ml is prepared, resulting in a total infusion volume of 250 ml. The infusion pump is pre-programmed with the required sequence of infusion steps.

Figure 12D:
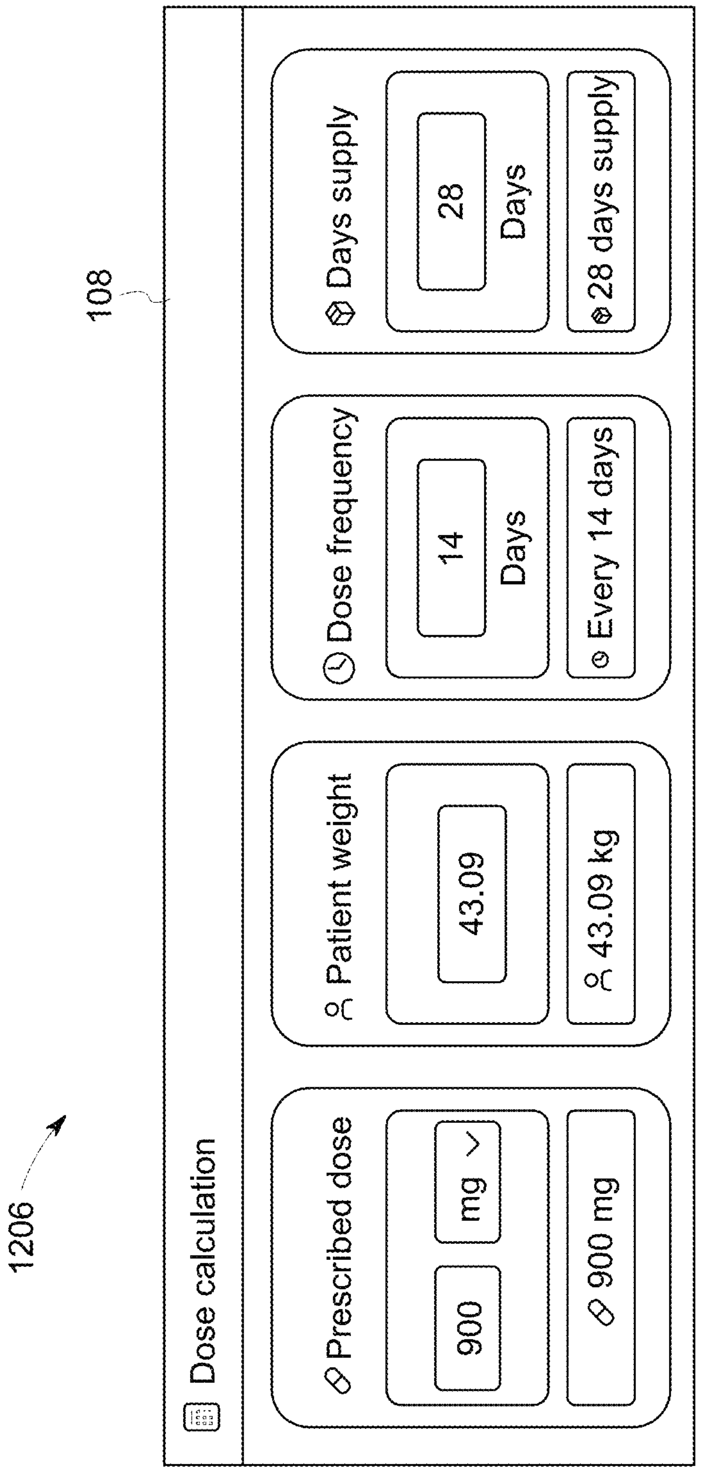

With reference to FIG. 12D, the dose evaluation module 110 is configured to calculate the required amount of the medication based on patient-specific inputs. The patient-specific inputs include, at minimum, the patient's body weight and the prescribed dosage.

The infusion pump programming system 100 further enables verification and adjustment of the computed infusion parameters through the user interface 108 prior to commencing the infusion to ensure compliance with the prescribed protocol.

To initiate the infusion, the pump is powered on to review the settings, the warm-up phase is allowed to complete, and the user presses "enter," followed by a second "enter" command to repeat the prescription. The pump automatically progresses through the programmed dosage steps. After priming and connecting the IV line, the user selects "Run" to begin the infusion. The programmed infusion protocol includes five steps: a first step administering 6.5 ml at a rate of 13 ml/hr for 30 minutes; a second step administering 19 ml at a rate of 38 ml/hr for 30 minutes; a third step administering 31.5 ml at a rate of 63 ml/hr for 30 minutes; a fourth step administering 183 ml at a rate of 88 ml/hr until completion; and a fifth step administering a 10 ml D5W flush at a rate of 88 ml/hr, wherein the flush is added to the additive port of the IV bag at the end of the fourth step. The total infusion time for this administration is approximately 3 hours and 41 minutes.

Figure 12E:
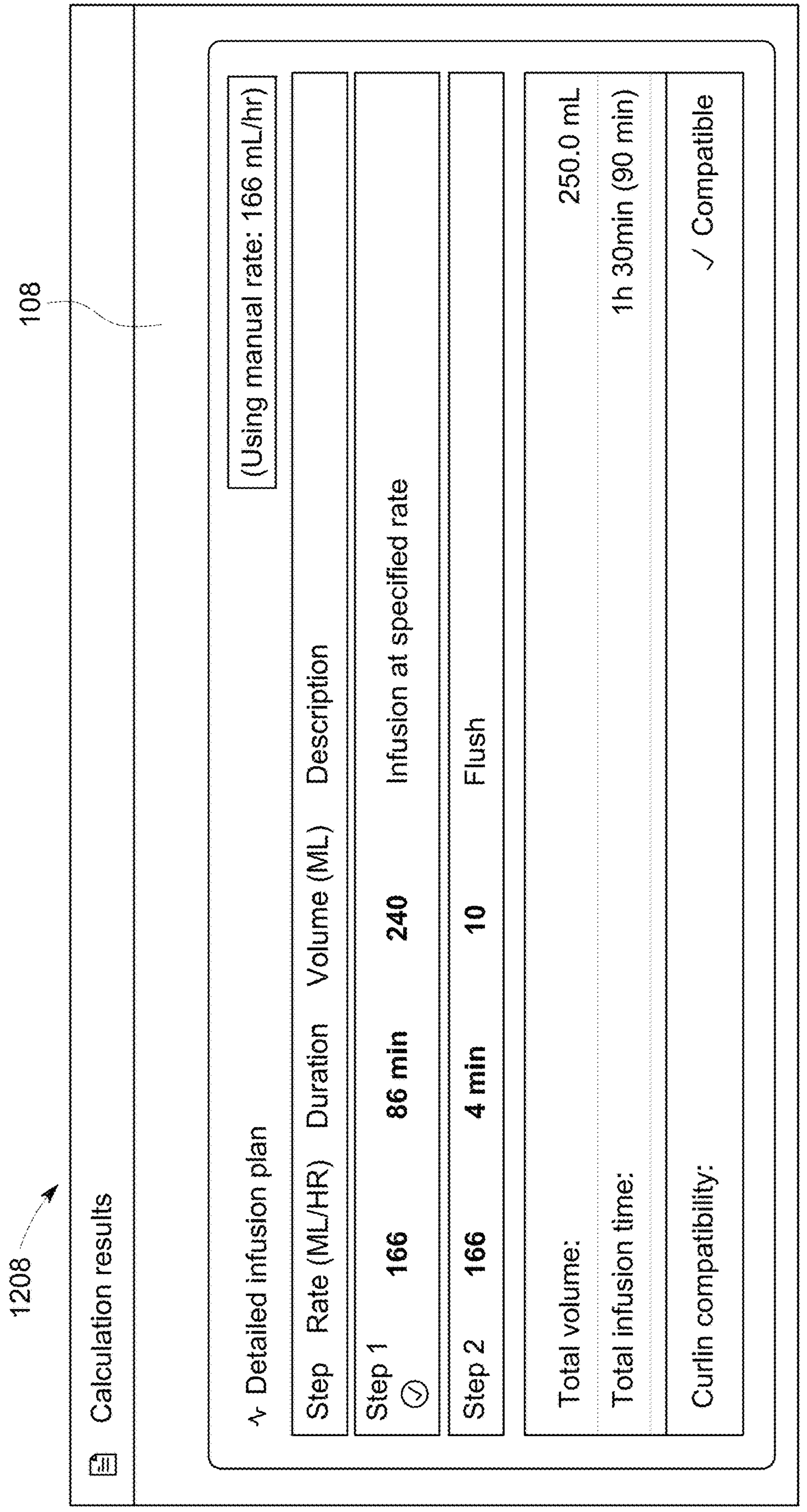

FIG. 12E illustrates an example layout 1208 of a calculated infusion plan generated by the infusion pump programming system 100 for a prescribed medication. The layout 1208 shows the detailed infusion steps, including the infusion rate, duration, and volume for each phase. In the illustrated example, the infusion plan comprises a first step in which 240 ml of the solution is infused at a rate of 166 ml/hr for a duration of 86 minutes, followed by a second step in which a 10 ml flush is infused at the same rate for 4 minutes. The interface further displays the total infusion volume of 250 ml, the calculated total infusion duration of 1 hour and 30 minutes, and a compatibility indicator confirming that the programmed infusion sequence is suitable for use with a Curlin infusion pump.

In one embodiment, certain infusion devices, including Curlin infusion pump, accept only discrete volume values ending in 0.0 or 0.5. Any calculated step volume that ends in a decimal between these values is considered non-conforming and cannot be entered into the device. Examples of valid and invalid values include: Valid: 100.0, 100.5, 247.0, 247.5. Invalid: 100.1, 100.3, 247.2, 247.8.

To ensure compatibility, the infusion pump programming system 100 implements an automatic decimal-adjustment algorithm. The algorithm identifies the decimal portion of the calculated volume and maps the value to the nearest acceptable increment. When the decimal portion falls between 0.1 and 0.4, the infusion pump programming system 100 normalizes the volume downward to the nearest integer, producing a 0.0 value. When the decimal portion falls between 0.6 and 0.9, the volume is normalized upward to the nearest 0.5 value. Following the adjustment, the infusion pump programming system 100 computes the volume difference between the original calculated volume and the normalized compliant volume. This difference is then reassigned to a compensation step, typically the immediately preceding step, in order to maintain strict volume conservation across the infusion protocol. The durations for both the adjusted step and the compensation step are then recalculated based on their respective rates, ensuring that rate-time-volume consistency is preserved.

In an exemplary embodiment, Before adjustment: Step 3:30.0 mL at 60 mL/hr→30.0 min. Step 4:247.3 mL at 88 mL/hr→168.5 min (non-compliant). Total: 277.3 mL. After applying decimal adjustment and redistribution: Step 3:29.8 mL at 60 mL/hr→29.8 min (compensated-0.2 mL). Step 4:247.5 mL at 88 mL/hr →168.8 min (compliant 0.5). Total: 277.3 mL (volume preserved). Temporal deviation is minimized (e.g., 0.2 mL adjustment results in approximately 12 seconds change).

The infusion pump programming system 100 employs a bidirectional redistribution mechanism to maintain volume integrity when a step volume is modified for device-compatibility. Upon identifying a non-conforming decimal and deriving the adjusted compliant volume, the infusion pump programming system 100 calculates the volume difference and redistributes this difference to an adjacent step, typically the step immediately preceding the adjusted step.

The compensation step's volume is then normalized to a precision of 0.1 mL, ensuring that the redistributed value does not introduce secondary decimal anomalies. Its duration is recalculated based on its infusion rate to preserve rate-time-volume coherence. The infusion pump programming system 100 additionally stores metadata indicating that the compensation was applied, enabling auditability, traceability, and downstream logic validation.

In another embodiment, the infusion pump programming system 100 applies a rule-based decimal adjustment protocol that aligns calculated volumes with device-specific constraints. The adjustment logic makes a determination based on the magnitude of the decimal component. When the decimal portion is less than 0.25, the value is rounded downward to the nearest whole number (ending in 0.0). When the decimal portion lies between 0.25 and 0.75, the value is rounded to the nearest 0.5 increment. When the decimal portion is 0.75 or greater, the value is rounded upward to the next whole number (ending in 0.0).

This decision tree ensures that all calculated infusion volumes conform to allowable device increments while minimizing the deviation from the originally computed volume. Any adjustments resulting from this rounding logic are compensated using the mechanisms.

In one embodiment, table 5 depicts rounding examples for device-compatible volume adjustment.

TABLE 5

| Original | Decimal | Decision | Adjusted | Difference |
|---|---|---|---|---|
| 247.1 | 0.1 | Round to .0 | 247.0 | −0.1 |
| 247.3 | 0.3 | Round to .5 | 247.5 | +0.2 |
| 247.5 | 0.5 | Keep .5 | 247.5 | 0.0 |
| 247.7 | 0.7 | Round to .0 | 248.0 | +0.3 |
| 247.9 | 0.9 | Round to .0 | 248.0 | +0.1 |

Figure 12F:
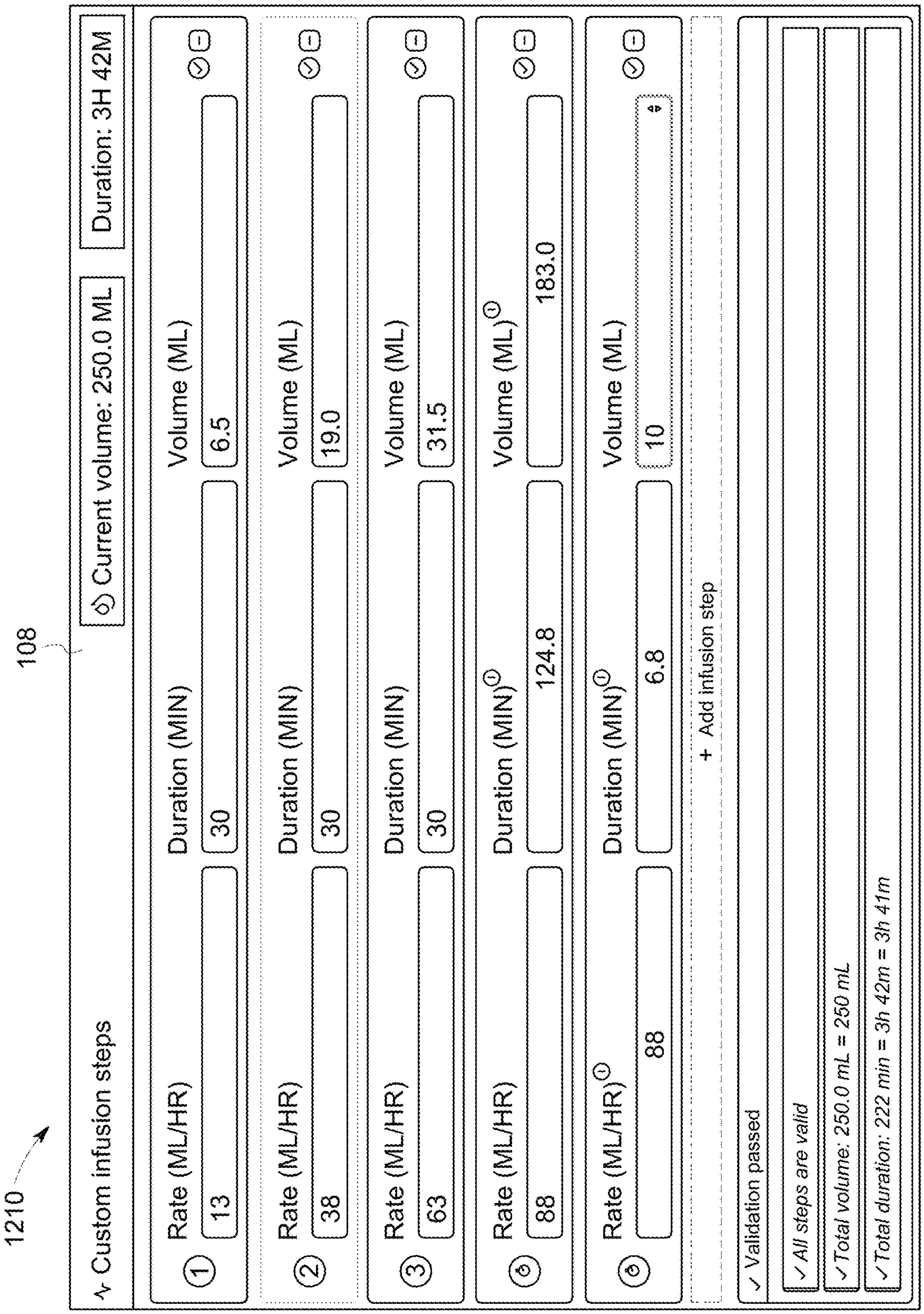

FIG. 12F illustrates the user interface 108 of the infusion pump programming system 100 enabling entry and customization of multi-step infusion parameters. The user interface 108 allows the user to specify infusion rate, duration, and corresponding volume for each step of the infusion protocol. The example shown depicts a five-step infusion sequence, with the first three steps configured at increasing rates of 13 ml/hr, 38 ml/hr, and 63 ml/hr, each for a duration of 30 minutes. A fourth step is configured at 88 ml/hr for delivery of 183 ml, and a final fifth step provides a 10 ml flush at 88 ml/hr. Validation results are displayed beneath the steps, confirming that all steps are valid, the cumulative volume equals 250 ml, and the total calculated infusion duration of 222 minutes (3 hours and 42 minutes) is consistent with the programmed parameters.

In another embodiment, the infusion pump programming system 100 that maintains a set of clinical constraints and, upon a change to any primary infusion parameter, automatically propagates that change throughout the protocol while respecting those constraints. The infusion pump programming system 100 that performs real-time, concurrent validation and optimization across multiple domains (safety, waste, pump compatibility) during the protocol creation process. The infusion pump programming system 100 that constructs a complex infusion protocol by selecting from a library of predefined "clinical phase templates" based on the context of the medication and patient.

In one embodiment, the infusion pump programming system 100 provides a comprehensive, bidirectionally coupled calibration and validation system that maintains total volume invariance, applies six-layer hierarchical validation, enforces deterministic rounding, and ensures smooth inter-step synchronization. This combination of algorithmic precision and clinical logic integration distinguishes the invention from prior approaches that treat infusion programming as a static calculation problem. The disclosed architecture thereby achieves real-time recalibration, mathematical accuracy, and regulatory-grade dose safety unattainable in existing systems.

In some embodiments, while embodiments described herein primarily relate to intravenous infusion therapy, the infusion pump programming system 100 is not limited to IV administration. The infusion pump programming system 100 is further applicable to multi-step therapeutic delivery protocols across various administration routes, including but not limited to subcutaneous, intramuscular, epidural, enteral, and transdermal delivery. The infusion pump programming system 100 may be configured to generate, recalibrate, and validate stepwise administration schedules for biologics, chemotherapeutics, parenteral nutrition, insulin titration, pain management therapy, anesthetic delivery, and other multi-phase treatment regimens that require controlled dose escalation, maintenance, tapering, or flushing phases.

In some embodiments, the infusion pump programming system 100 is operatively linked with infusion pumps and external medication delivery devices to enable automatic programming of recalibrated infusion parameters. The machine-readable code generated by the infusion pump programming system 100 may be configured for direct ingestion by an infusion pump via scanning, wireless transfer, or data import using HL7, FHIR, Bluetooth, Wi-Fi, NFC, RFID, or serial communication protocols. Upon import, the infusion pump may automatically configure stepwise rate, volume, and duration parameters based on the recalibrated protocol, thereby reducing manual pump programming burden and further minimizing the risk of bedside transcription errors.

In some embodiments, the infusion pump programming system 100 is configured to perform real-time adaptive recalibration during an ongoing infusion. The infusion pump programming system 100 may receive physiological or clinical feedback data such as heart rate, blood pressure, oxygen saturation, adverse reaction alerts, or clinician override commands and automatically adjust infusion step parameters in response. This real-time recalibration maintains clinical logic and safety rules while dynamically modifying the infusion sequence to mitigate potential adverse events, thus enabling continuous closed-loop or semi-automated control of therapeutic delivery.

In some embodiments, beyond safety range detection, the machine learning module may be configured to provide predictive and prescriptive intelligence for infusion therapy optimization. The AI engine may analyze historical infusion outcomes, patient-specific variables, adverse event records, and dosing efficiency trends to recommend optimal infusion patterns, vial selections, rate transition curves, or dilution strategies. In some embodiments, a reinforcement learning framework may refine infusion calibration recommendations over time based on aggregated clinical usage data, thereby enabling self-improving dosing models tailored to medication, clinical indication, or patient cohorts.

In some embodiments, the infusion pump programming system 100 may be implemented as a cloud-based enterprise platform for centralized management of medication formularies, infusion protocols, and calibration records across multiple departments, sites, or healthcare institutions. The infusion pump programming system 100 may maintain audit logs, version control, digital signatures, and regulatory compliance metadata (e.g., FDA 21 CFR Part 11, EU Annex 11), enabling uniform protocol governance, traceability, and cross-site standardization. Integration with EMR/EHR and pharmacy information systems via HL7/FHIR enables automatic retrieval of physician orders and bi-directional data exchange for hospital workflow automation.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principles of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

It will readily be apparent that numerous modifications and alterations can be made to the processes described in the foregoing examples without departing from the principles underlying the invention, and all such modifications and alterations are intended to be embraced by this application.

The claimed invention is:

1. An infusion pump programming system with automated dose evaluation, real-time infusion rate calibration, and safety validation, comprising:

an infusion pump configured to provide infusion to a patient;

a server comprising a database which stores medication identifiers, vial sizes, vial strength values, standardized dosing protocols, a predetermined clinical step hierarchy, infusion safety limits, clinical dosing limits, and pediatric, adult, renal-adjusted, and condition-specific dosing protocols;

a computing device operatively coupled to the infusion pump and the server via a network and configured to generate pump-executable infusion commands, wherein the computing device comprises a user interface, a processor, and a memory, the memory storing instructions that are executed by the processor, wherein the computing device is communicatively coupled with a server via a network, wherein the server comprises a database, which stores medication identifiers, vial strengths, standardized dosing protocols, infusion safety limits, and pediatric, adult, renal-adjusted, and condition-specific dosing protocols, wherein the instructions executed by the processor are configured to cause the processor to:

receive, by the user interface, input parameters that include patient information including patient-specific data and infusion parameters evaluation, wherein the infusion parameters comprise at least one of total infusion volume and total infusion time;

execute a protocol generation module to generate an initial infusion protocol based on the input parameters and comprising at least one of a fixed-rate infusion protocol and a multi-step variable-rate infusion protocol based on the infusion parameters, wherein the generated initial infusion protocol comprises a plurality of infusion steps and is based on the patient-specific data, wherein the plurality of infusion steps are stored in the memory in a defined sequential order representing a clinical infusion sequence that includes a pre-infusion flush, one or more ramp-up steps, a main infusion step, one or more ramp-down steps, and a post-infusion flush, wherein each infusion step is stored in a data structure in the memory, the data structure defining at least two of an infusion rate, a duration, and a calculated total infusion volume for the received at least one of total infusion volume and total infusion time, wherein the total infusion volume is calculated from the stored infusion steps in the event the received infusion parameters comprise total infusion time;

receive, by a calibration module, a calibration command selecting at least one of a rate calibration mode in which a new infusion rate is applied and a time calibration mode in which a new total infusion duration is applied;

recalculate, by the calibration module, the infusion rate, duration, and/or volume parameters of the plurality of infusion steps based on the selected calibration mode, thus defining a recalibrated infusion protocol, by accessing the data structure for the plurality of infusion steps and using a single-pass convergence process, wherein the single-pass convergence process produces, in a single computational traversal, recalibrated infusion rate and duration values for the selected mode using non-iterative closed-form equations, thereby preventing floating-point drift and eliminating intermediate unsafe states, wherein the single-pass convergence comprises computing a plurality of recalibrated rates and duration values in the single, non-iterative traversal using the closed-form equations, wherein in the rate calibration mode is configured to recalculate the duration for one or more each of the plurality of infusion steps based on the recalibrated infusion rate while holding the calculated volume for each step constant, thereby modifying the total infusion duration time for each step while preserving the total infusion volume and the defined sequential order, wherein in the time calibration mode is configured to recalculate the infusion rate for one or more each of the plurality of infusion steps based on the modified total infusion duration time while holding the calculated volume for each step constant, thereby modifying the infusion rate for each step while preserving the total infusion volume and the defined sequential order, and wherein the recalculating maintains the predetermined clinical step hierarchy among the ramp-up steps, the main infusion step, and the ramp-down steps, the predetermined clinical step hierarchy being stored in and accessed from the database and defining the role of each step within a sequence based on its relative position in the sequence, wherein the predetermined clinical step hierarchy comprises pre-infusion flush, ramp-up, main infusion, ramp-down, and post-infusion flush, perform, by wherein the calibration module, performs device-compatibility rounding of step volumes to 0.0 or 0.5 mL increments and redistribute the any resulting volume difference to a designated compensation step while maintaining total-volume invariance;

execute a validation module that validates the recalibrated infusion protocol for clinical safety and mathematical consistency by comparing the recalculated infusion rates against the infusion safety limits stored in and accessed from the database and by verifying, prior to execution of the recalibrated infusion protocol, that a cumulative volume of the plurality of infusion steps matches a prescribed the total infusion volume prior to execution;

determine and display a validation status with specific error messages on the user interface when the cumulative volume is mismatched with the prescribed total infusion volume; and execute a document generation module to generate an infusion output that is displayed on the user interface and that includes the patient information, the recalibrated infusion protocol parameters, and a graphical code, wherein the graphical code encodes a structured data payload of the plurality of infusion steps for the recalibrated infusion protocol, wherein the processor generates a pump-executable control-register sequence and writes recalibrated rate, duration, and step-transition parameters directly into device-specific infusion-pump registers in a single atomic update, thereby preventing transient unsafe intermediate states during reprogramming, wherein the single atomic update comprises simultaneous updating of the main infusion rate and flush rate such that no intermediate mismatched values are stored in memory, control, by the processor, the infusion pump to execute the pump-executable control-register sequence and provide infusion to the patient.

2. The infusion pump programming system of claim 1, wherein the server is further configured to store historical infusion data and provide version control of the generated infusion protocols.

3. The infusion pump programming system of claim 1, wherein the infusion pump programming system further comprises a vial preparation assistance module that is integrated with the protocol generation module and is configured to:

receive a required dose value for a selected medication;

retrieve available medication vial sizes and strength values from the database;

automatically select, based on pump-programming and dose-safety constraints, one or more vial combinations that provide a medication amount meeting a predetermined accuracy range required by the infusion pump programming system;

compute, for each selectable vial combination, a deliverable drug amount and a corresponding infusion-pump dose parameter that must be programmed into the infusion pump registers;

verify that the deliverable drug amount falls within clinical dosing limits stored in the database and that the resulting infusion-pump rate and duration values remain within device-safe ranges; and provide, to the user interface, a system-validated vial selection that is compatible with the generated infusion protocol and ready for translation into pump-executable control-register values, wherein the vial preparation assistance module constrains vial selection to combinations that satisfy pump-device requirements for minimum measurable volume, minimum programmable rate, infusion-time tolerances, and drug-stability duration, thereby producing only clinically usable and pump-compatible vial configurations, wherein a vial optimization module implements a multi-strategy dynamic optimization engine configured to:

generate vial combinations using four parallel optimization strategies simultaneously;

rank combinations using dual-criteria global optimization prioritizing waste minimization primarily and vial count reduction secondarily;

integrate supply-period optimization across entire treatment duration;

employ intelligent thresholds triggering alternative suggestions at 20% waste and optimize accuracy boundaries; and utilize precision remainder detection with 0.01 clinical significance threshold.

4. The infusion pump programming system of claim 1, wherein the protocol generation module is further configured to determine a missing infusion parameter when any two of infusion rate, infusion volume, and infusion duration are provided, by applying a triangular computational relationship.

5. The infusion pump programming system of claim 1, wherein the validation module provides visual indicators that comprise a green check for valid parameters and a red warning symbol for invalid parameters, wherein the validation module performs multilayer validation including at least input, formula, and volume consistency checks.

6. The infusion pump programming system of claim 1, wherein the validation module is further configured to apply tolerance limits of ±0.1 mL for total volume and ±1 minute for total infusion duration, wherein cumulative rounding error across all recalibrated steps is maintained within ±0.1 mL.

7. The infusion pump programming system of claim 1, wherein the calibration module is further configured to receive the calibration command from a mode selector, which is configured to enable a user to select between the rate calibration mode and the time calibration mode, wherein the calibration module implements the single-pass convergence through constraint enforcement during calculation construction, wherein the infusion pump programming system is configured to:

explicitly lock medication volumes before parameter adjustment;

enforce time distribution exactness through mathematical derivation; and apply rate synchronization through atomic assignment, wherein the processor performs atomic rate synchronization by simultaneously assigning an identical recalibrated rate to both the main infusion step and the post-flush step, wherein all validation criteria are satisfied by construction during a single computational pass without requiring iterative refinement.

8. The infusion pump programming system of claim 1, wherein the calibration module performs an atomic assignment that simultaneously writes the same infusion rate value to both the main infusion step and the flush step.

9. The infusion pump programming system of claim 1, wherein the calibration module performs deterministic bottom-up aggregation by computing total duration and total volume exclusively from individual step parameters, thereby eliminating floating-point drift.

10. The infusion pump programming system of claim 1, wherein the document generation module generates a document containing a QR code encoding the recalibrated infusion protocol parameters in a structured data format.

11. The infusion pump programming system of claim 1, wherein the infusion pump programming system further comprises a dose evaluation module configured to compute a required drug amount based on patient-specific data, wherein the patient-specific data comprises at least patient weight and prescribed dose.

12. The infusion pump programming system of claim 1, wherein the infusion pump programming system is further configured to enable dynamic insertion of additional infusion steps, and upon adding a new step, wherein the processor automatically assigns a sequential step number, allocates default parameter values for rate, volume, and duration based on step type, and recalculates overall protocol sequencing to maintain correct clinical order.

13. The infusion pump programming system of claim 1, wherein the user interface is configured to display a validation passed message upon successful verification of the infusion protocol, wherein the message comprises:

confirmation that all infusion steps are valid, a total volume evaluation showing equivalence between a sum of step volumes and target infusion volume, and a total duration evaluation showing equivalence between a sum of step durations and expected total infusion time.

14. A computer-implemented method for recalibrating multi-step infusion protocols using an infusion pump programming system, comprising:

providing, as part of the infusion pump programming system, an infusion pump configured to provide infusion to a patient;

providing, as part of the infusion pump programming system, a computing device operatively coupled to the infusion pump and comprising a user interface, a processor, and a memory, the computing device performing the steps comprising:

storing, in the memory, an initial infusion protocol comprising a plurality of steps in a defined sequential order, each step having a step type classified as one of a pre-infusion flush, a ramp-up step, a main infusion step, a ramp-down step, and a post-infusion flush, wherein each step defines at least two of an infusion rate, a duration, and a total infusion volume;

receiving, by the user interface, patient-specific data and infusion setup parameters, wherein the infusion setup parameters comprise at least one of total infusion volume and total infusion time;

executing a dose evaluation module to compute the total initial infusion rate, volume, and duration based on the patient-specific data and infusion setup parameters;

generating, by a protocol generation module, an initial infusion protocol for at least one of a fixed-rate infusion protocol and a multi-step variable-rate infusion protocol based on the infusion parameters from the memory, wherein the generated initial infusion protocol comprises a plurality of infusion steps and is based on the patient-specific data;

receiving, by a calibration module, a calibration command by the user interface selecting at least one of a rate calibration mode in which a new infusion rate is applied and a time calibration mode in which a new total infusion duration is applied;

recalculating, by the calibration module, the infusion rate, duration, and/or volume parameters of the plurality of infusion steps based on the selected calibration mode and the new infusion rate or new total infusion duration by accessing a data structure for the plurality of infusion steps stored in the memory, thus creating a recalibrated infusion protocol;

implementing, by the protocol generation module, a triangular computational relationship such that any change to either rate, volume, or duration triggers automatic reevaluation of a dependent parameter to maintain mathematical integrity of the generated infusion protocol, wherein in the rate calibration mode is configured to recalculate the duration for each of the plurality of infusion steps based on the new infusion rate while holding the calculated volume for each step constant, thereby modifying the total infusion time for each step while preserving the total infusion volume and the defined sequential order, wherein in the time calibration mode is configured to recalculate the infusion rate each of the plurality of infusion steps based on the new total infusion duration while holding the calculated volume for each step constant, thereby modifying the infusion rate for each step while preserving the total infusion volume and the defined sequential order;

performing, by the calibration module, device-compatibility rounding of step volumes to 0.0 or 0.5 mL increments and redistributing the any resulting volume difference to a designated compensation step while maintaining total-volume invariance;

validating, by a validation module, the recalibrated infusion protocol for dose safety and infusion accuracy by checking recalculated parameters against infusion safety limits stored in the memory;

providing, by a document generation module, the recalibrated infusion protocol in an infusion output that includes patient information stored in the memory, the recalibrated infusion protocol parameters, and a graphical code; and controlling, by the processor, the infusion pump to execute the recalibrated infusion protocol and provide infusion to the patient.

15. The method of claim 14, wherein the protocol generation module automatically determines a missing infusion parameter when any two of infusion rate, infusion volume, and infusion duration are provided as part of the initial infusion protocol.

16. The method of claim 14, wherein the infusion pump programming system further comprises a server, which is operatively coupled to the computing device and is configured to store historical infusion data and provides version control of the generated infusion protocols.

17. The method of claim 14, wherein the validation module provides visual indicators that comprise a green check for valid parameters and a red warning symbol for invalid parameters.

18. The method of claim 14, wherein the infusion pump programming system comprises a document generation module generates a document containing a QR code encoding the recalibrated infusion protocol parameters in a structured data format.

* * * * *